(12) United States Patent
Sakuma et al.

(10) Patent No.: US 9,427,402 B2
(45) Date of Patent: Aug. 30, 2016

(54) PREPARATION FOR IMPROVING SOLUBILITY OF POORLY SOLUBLE DRUG

(75) Inventors: Satoshi Sakuma, Amagasaki (JP); Hiroshi Ueda, Toyonaka (JP); Akira Mashimo, Amagasaki (JP); Hiroshi Murazato, Osaka (JP)

(73) Assignee: Shionogi & Co. Ltd., Osaka (JP)

( * ) Notice: Subject to any disclaimer, the term of this patent is extended or adjusted under 35 U.S.C. 154(b) by 0 days.

(21) Appl. No.: 13/825,552

(22) PCT Filed: Sep. 29, 2011

(86) PCT No.: PCT/JP2011/072355
§ 371 (c)(1),
(2), (4) Date: Mar. 21, 2013

(87) PCT Pub. No.: WO2012/043709
PCT Pub. Date: Apr. 5, 2012

(65) Prior Publication Data
US 2013/0203723 A1 Aug. 8, 2013

(30) Foreign Application Priority Data

Sep. 30, 2010 (JP) .................. 2010-221000

(51) Int. Cl.
*A61K 9/00* (2006.01)
*A61K 9/20* (2006.01)
(Continued)

(52) U.S. Cl.
CPC .......... *A61K 9/0053* (2013.01); *A61K 9/1611* (2013.01); *A61K 9/1617* (2013.01); *A61K 9/1623* (2013.01); *A61K 9/1652* (2013.01); *A61K 9/2054* (2013.01); *A61K 9/2077* (2013.01); *A61K 31/405* (2013.01); *A61K 31/426* (2013.01)

(58) Field of Classification Search
None
See application file for complete search history.

(56) References Cited

U.S. PATENT DOCUMENTS 5,028,433 A 7/1991 Ishimaru et al.
5,631,296 A 5/1997 Birrenbach et al.
(Continued)

FOREIGN PATENT DOCUMENTS

CA 2 623 018 5/2007
EA 003663 B1 8/2003
(Continued)

OTHER PUBLICATIONS

Fotaki et al. "rationale for selection of dissolution", Dissolution Technologies, Aug. 2013, pp. 6-13.*
(Continued)

*Primary Examiner* — Ernst V Arnold
*Assistant Examiner* — Kyung Sook Chang
(74) *Attorney, Agent, or Firm* — Finnegan, Henderson, Farabow, Garrett and Dunner, L.L.P.

(57) ABSTRACT

The present invention relates to solubility improving preparation for enhancing the oral absorption of a poorly soluble drug, which is comprising (A) and (B);
(A) a granulated substance which comprises
(i) a poorly soluble drug having an acidic group in the molecule,
(ii) an alkaline agent,
(iii) a surfactant,
and this granulated substance dose not substantially contain a disintegrator,
(B) a disintegrator existing only in the external of the granulated substance.

20 Claims, 6 Drawing Sheets

(51) Int. Cl.
    *A61K 9/16*     (2006.01)
    *A61K 31/405*   (2006.01)
    *A61K 31/426*   (2006.01)

(56) References Cited

U.S. PATENT DOCUMENTS

| | | |
|---|---|---|
| 6,951,657 B1 | 10/2005 | Zuccarelli et al. |
| 2006/0078609 A1 | 4/2006 | Vandecruys et al. |
| 2008/0286344 A1* | 11/2008 | Darmuzey ........... A61K 9/2054 424/443 |
| 2009/0175940 A1 | 7/2009 | Gruber |
| 2010/0267783 A1 | 10/2010 | Takayama et al. |

FOREIGN PATENT DOCUMENTS

| | | |
|---|---|---|
| EA | 004803 B1 | 8/2004 |
| EP | 0 607 467 | 7/1994 |
| EP | 1 008 354 | 6/2000 |
| EP | 1 797 872 | 6/2007 |
| JP | 47-10498 | 5/1972 |
| JP | 3-240729 | 10/1991 |
| JP | 9-202728 | 8/1997 |
| JP | 2006-514635 | 5/2006 |
| JP | 2010-189337 | 9/2010 |
| WO | WO 98/29137 | 7/1998 |
| WO | WO99/09958 | 3/1999 |
| WO | WO99/09959 | 3/1999 |
| WO | WO 2004/028505 | 4/2004 |
| WO | WO 2004/050068 | 6/2004 |
| WO | WO 2004/087096 | 10/2004 |
| WO | WO 2005/030257 | 4/2005 |
| WO | WO 2007/061415 | 5/2007 |
| WO | WO 2007/072060 | 6/2007 |
| WO | WO 2009017098 A1 * | 2/2009 |
| WO | WO 2009/048940 | 4/2009 |
| WO | WO 2010/033179 | 3/2010 |
| WO | WO 2010/095494 | 8/2010 |

OTHER PUBLICATIONS

Park et al. "The effects of surfactants on the dissolution profiles of poorly water-soluble acidic drugs", Int'l Journal of Pharmaceuticals, 2006, pp. 35-41.*

He et al., "Development of a rapidly dispersing tablet of a poorly wettable compound . . . ", International Journal of Pharmaceutics 353 (2008), pp. 176-186.*

Gordon et al., "Effect of the mode of super disintegrant incorporation on dissolution in wet granulated tablets", Institute of Pharmaceutical Science, Syntex, Inc., (1992), pp. 220-226.*

Scifinder—cas resgistry No. 1110766-97-6, accessed Nov. 17, 2015.*

English-language International Search Report from the Japanese Patent Office in International Application No. PCT/2011/072355 mailed Oct. 25, 2011.

Notification of Transmittal of Translation of the International Preliminary Report on Patentability, International Preliminary Report on Patentability, and Translation of the Written Opinion of the International Searching Authority, for International Patent Application No. PCT/JP2011/072355, mailed Apr. 18, 2013 (7 pages).

English-language Abstract for JP 2010-189337, dated Sep. 2, 2010.

Supplementary European Search Report EP 11 829 262.2; mailed Feb. 26, 2014.

Scifinder—CAS Registry No. 144701-48-4, accessed May 26, 2015.

Carter, John C., "The Role of Disintegrants in Solid Oral Dosage Manufacturing", Carter Pharmaceutical Consulting Inc., pp. 1-3 (2002-2006).

* cited by examiner

PREPARATION FOR IMPROVING SOLUBILITY OF POORLY SOLUBLE DRUG

TECHNICAL FIELD

The present invention relates to a solubility improving preparation for enhancing the oral absorption of a poorly soluble drug, a method for producing the preparation and a method for improving solubility.

BACKGROUND ART

When a poorly soluble drug having a polar group in the molecule is orally administered, oral absorption may in some cases be reduced due to low solubility in the pH condition in the gastrointestinal tract. In particular, many of the compounds having an acidic group in the molecule lose solubility as the pH become lower and result in poor solubility. Thus, when such compounds are orally administered, they are not efficiently dissolved from the preparation in the stomach, or they soon precipitate even when they are once dissolved. The low oral absorption has been the problem.

A method of forming solid dispersions is known as a method for improving the oral absorption of a poorly soluble drug. However, solid dispersions are produced by supporting a refined poorly soluble drug in a substrate, thus the poorly soluble drug exists in an amorphous state in the solid dispersions, and the surface energy of the particles is high. Thus, the solid dispersions have poor physical stability (non-patent document 1). Moreover, in the case of solid dispersions, a disintegrator such as conventional croscarmellose calcium or low substituted hydroxypropyl cellulose alone cannot exhibit sufficient disintegration (patent document 1).

Accordingly, a method other than forming solid dispersions is expected to be developed as a method for improving the oral absorption of a poorly soluble drug.

Various studies have been conducted to find other methods to improve the solubility of a poorly soluble drug. For example, when the poorly soluble drug is a compound having an acidic group in the molecule, (1) a preparation having improved solubility by making the poorly soluble drug an salt (patent document 2) and (2) a preparation having improved solubility by creating an alkali environment in the vicinity of the poorly soluble drug by compounding an alkali agent (patent documents 3 to 5, non-patent document 2), and the like have been reported.

However, patent document 2 states that, even though the solubility to water with a pH of 7 is improved by making the poorly soluble drug a salt, precipitation of the drug may be triggered by the acidic pH condition of the stomach after oral administration.

The preparation described in patent document 3 is produced by adding from outside an alkali agent to a granulated substance containing a poorly soluble drug. Likewise, the preparation described in non-patent document 2 is produced by directly tablet-compressing a mixture comprising a poorly soluble drug and an alkali agent, thus an alkali environment needs to be created in the entire preparation, as compared to the case where an alkali environment is created only inside the granulated substance by compounding an alkaline agent exclusively into the inside of the granulated substance containing the poorly soluble drug. Thus, each of the preparations described in the documents stated above needs to compound a large amount of alkali agent to be a preparation of a drug with especially high poor solubility, and thus it is not an adequate preparation.

Moreover, the preparations described in patent documents 4 and 5 are produced by granulating a poorly soluble drug, an alkaline agent and a disintegrator in a lump, thus at the time of disintegration when the granulated substance itself disintegrates, there is a possibility that the alkaline agent disperses from the vicinity of the poorly soluble drug and the environment adequate for dissolving the poorly soluble drug may be lost.

PRIOR TECHNICAL DOCUMENTS

Patent Documents

Patent Document 1: WO 98/29137 A1
Patent Document 2: WO 2006/100281 A1
Patent Document 3: WO 2009/048940 A1
Patent Document 4: WO 2007/061415 A1
Patent Document 5: JP 3-240729

Non-Patent Documents

Non-patent Document 1: "Design and Evaluation of Orally Administration Preparation", p. 178, 1995
Non-patent Document 2: "Journal of Pharmaceutical Science and Technology, Japan", Vol. 69, No. 5, pp. 329-335, 2009

SUMMARY OF THE INVENTION

Problem to be Solved by the Invention

The objective of the present invention is to provide a preparation with improved solubility of a poorly soluble drug, and, as a result, with improved oral absorption.

Means to Solve the Problem

The inventors of the present invention found that a preparation with an improved solubility of a poorly soluble drug could be produced by mixing a disintegrator with a granulated substance comprising the poorly soluble drug having a polar group (an acidic group or a basic group) in the molecule, a pH adjuster (an alkaline agent or an acid), and a surfactant, and achieved the following invention (hereinafter referred to also as a "solubility improving preparation of the present invention").

(1) A solid preparation comprising (A) and (B);
(A) a granulated substance which comprises
(i) a poorly soluble drug having an acidic group in the molecule,
(ii) an alkaline agent,
(iii) a surfactant,
and this granulated substance dose not substantially contain a disintegrator,
(B) a disintegrator existing only in the external of the granulated substance,
(2) The solid preparation according to (1), wherein the acidic group is one or more selected from the group consisting of carboxyl group, sulfo group, sulfino group, phosphono group and phenolic hydroxy group,
(3) The solid preparation according to (2), wherein the acidic group is carboxyl group,
(4) The solid preparation according to (3), wherein the poorly soluble drug is an optically active compound represented by Formula (I):

[Chemical formula 1]

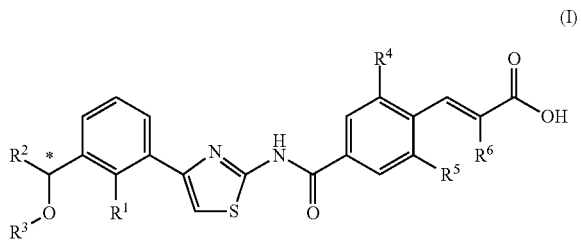

wherein, R1 is halogen atom or C1-C3 alkyloxy; R2 is C1-C8 alkyl; R3 is C1-C8 alkyl; R4 and R5 are each independently fluorine atom or chlorine atom; R6 is C1-C3 alkyl or C1-C3 alkyl oxy; and carbon atom with "*" attached to it is an asymmetric carbon, its pharmaceutically acceptable salt, or solvate thereof, (5) The solid preparation according to (4), wherein the poorly soluble drug is (S)-(E)-3-(2,6-dichloro-4-{4-[3-(1-hexyloxyethyl)-2-methyloxyphenyl]thiazole 2-yl carbamoyl}phenyl)-2-methylacrylic acid, its pharmaceutically acceptable salt, or solvate thereof, (6) The solid preparation according to (3), wherein the poorly soluble drug is nonsteroidal anti-inflammatory drug or bile acid, (7) The solid preparation according to (3), wherein the poorly soluble drug is one or more selected from the group consisting of indomethacin, ibuprofen, mefenamic acid and ursodeoxycholic acid, (8) The solid preparation according to any one of (1) to (7), wherein the alkaline agent is one or more compounds containing in the molecules one or more selected from the group consisting of magnesium, calcium, and aluminum, (9) The solid preparation according to (8), wherein the alkaline agent is one or more selected from the group consisting of magnesium oxide, magnesium hydroxide, hydroxylation alumina magnesium, synthetic hydrotalcite, calcium carbonate, magnesium carbonate, and calcium silicate,

(10) The solid preparation according to (9), wherein the alkaline agent is magnesium oxide and/or magnesium hydroxide,

(11) The solid preparation according to (10), wherein 0.5 to 30 weight % of magnesium oxide and/or 0.5 to 30 weight % of magnesium hydroxide are contained as alkaline agents based on the said granulated substance,

(12) The solid preparation according to any one of (1) to (11), wherein the surfactant is an ionic surfactant,

(13) The solid preparation according to (12), wherein the ionic surfactant is a sulfuric acid ester salt,

(14) The solid preparation according to (13), wherein the sulfuric acid ester salt is a sodium lauryl sulfate,

(15) The solid preparation according to (14), wherein 0.2 to 50 weight % of the sodium lauryl sulfate is contained based on the said granulated substance,

(16) The solid preparation according to any one of (1) to (15) wherein the disintegrator is one or more selected from the group consisting of cellulosic derivative, polyvinyl pyrrolidone derivative and starch derivative,

(17) The solid preparation according to (16), wherein the disintegrator is one or more selected from the group consisting of low substituted hydroxypropyl cellulose, carmellose calcium, crospovidone, and carboxymethyl starch sodium,

(18) The solid preparation according to (17), wherein 0.2 to 30 weight % of carmellose calcium is contained based on the said solid preparation,

(19) The solid preparation according to (18), wherein 3 to 7 weight % of carmellose calcium is contained based on the said solid preparation,

(20) The solid preparation according to any one of (1) to (19), wherein the granulated substance contains hydroxypropyl cellulose,

(21) The solid preparation according to (20), wherein 0.1 to 20 weight % of hydroxypropyl cellulose is contained based on the said granulated substance,

(22) The solid preparation according to any one of (1) to (4), (6) to (18), (20) and (21), wherein 0.5 to 30 weight % of magnesium oxide, 0.5 to 30 weight % of magnesium hydroxide, 0.2 to 50 weight % of sodium lauryl sulfate and 0.1 to 20 weight % of hydroxypropyl cellulose are contained based on the said granulated substance, wherein 0.2 to 30 weight % of carmellose calcium is contained as disintegrator based on the said solid preparation,

(23) The solid preparation according to (22), wherein the poorly soluble drug is (S)-(E)-3-(2,6-dichloro-4-{4-[3-(1-hexyloxyethyl)-2-methyloxyphenyl]thiazole 2-yl carbamoyl}phenyl)-2-methylacrylic acid, its pharmaceutically acceptable salt or solvate thereof,

(24) The solid preparation according to (22) or (23), wherein 3 to 7 weight % of carmellose calcium is contained in the solid preparation,

(25) The solid preparation according to any one of (1) to (24), wherein the solubility of the poorly soluble drug in any solvent with a pH of 7 or less at 37° C. is 1 mg/ml or less,

(26) The solid preparation according to any one of (1) to (25), wherein the solubility of the poorly soluble drug in a solvent with a pH of 4 at 37° C. is 1 mg/ml or less,

(27) The solid preparation according to any one of (1) to (26), wherein the solubility of the poorly soluble drug in a solvent with a pH of 7 at 37° C. is 1 mg/ml or less,

(28) A solid preparation comprising (A) and (B);
  (A) a granulated substance which comprises
    (i) a poorly soluble drug having a basic group in the molecule,
    (ii) an acid
    (iii) a surfactant,
    and this granulated substance dose not substantially contain a disintegrator,
  (B) a disintegrator existing only in the outside of the granulated substance,

(29) The solid preparation according to any one of (1) to (28), wherein the solid preparation form is tablet or capsule,

(30) The solid preparation according to any one of (1) to (29), wherein the solid preparation form is tablet,

(31) A process for producing the solid preparation according to any one of (1) to (27), (29) and (30) containing:
  (A) mixing
    (i) a poorly soluble drug having an acidic group in the molecule,
    (ii) an alkaline agent
    (iii) a surfactant, and granulating the mixture,
  (B) mixing the granulated substance prepared in (A) with a disintegrator,

(32) A method for improving the solubility of a poorly soluble drug having an acidic group in the molecule, wherein the method contains (A) mixing
    (i) a poorly soluble drug having an acidic group in the molecule,
    (ii) an alkaline agent,
    (iii) a surfactant,
and granulating the mixture,
(B) mixing the granulated substance prepared in (A) with a disintegrator,

(33) A granulated substance comprising (S)-(E)-3-(2,6-dichloro-4-{4-[3-(1-hexyloxyethyl)-2-methyloxyphenyl]thiazole 2-yl carbamoyl}phenyl)-2-methylacrylic acid, a surfactant and an alkaline agent,

(34) The granulated substance according to (33), wherein the surfactant is an ionic surfactant,

(35) The granulated substance according to (34), wherein the ionic surfactant is sodium lauryl sulfate.

(36) The granulated substance according to any one of (33) to (35), wherein the alkaline agent is magnesium oxide, magnesium hydroxide, or a mixture thereof,

(37) A solid preparation comprising a granulated substance according to any one of (33) to (36),

(38) The solid preparation according to any one of (1) to (30) and (37), wherein the dissolution rate after 60 minutes the dissolution test begins is 20% or more in the dissolution test using the 2nd fluid of the Japanese Pharmacopoeia Disintegration Test applying Method 2 (Paddle method) of the 14th edition of Japanese Pharmacopoeia Dissolution Test,

(39) The solid preparation according to any one of (1) to (30) and (37), wherein the dissolution rate after 60 minutes the dissolution test begins is four times or more as much as the dissolution rate of a bulk powder or a mixture powder containing the bulk powder.

Effect of the Invention

The solubility improving preparation of the present invention exhibits high solubility even under a pH condition where a poorly soluble drug is intrinsically poorly soluble. Accordingly, the solubility of the solubility improving preparation of the present invention is little affected by the pH condition in the gastrointestinal tract, and thus is expected to exhibit high oral absorption in a large area from the stomach to the upper portion of the small intestine.

EMBODIMENTS FOR CARRYING OUT THE INVENTION

Figure 1:
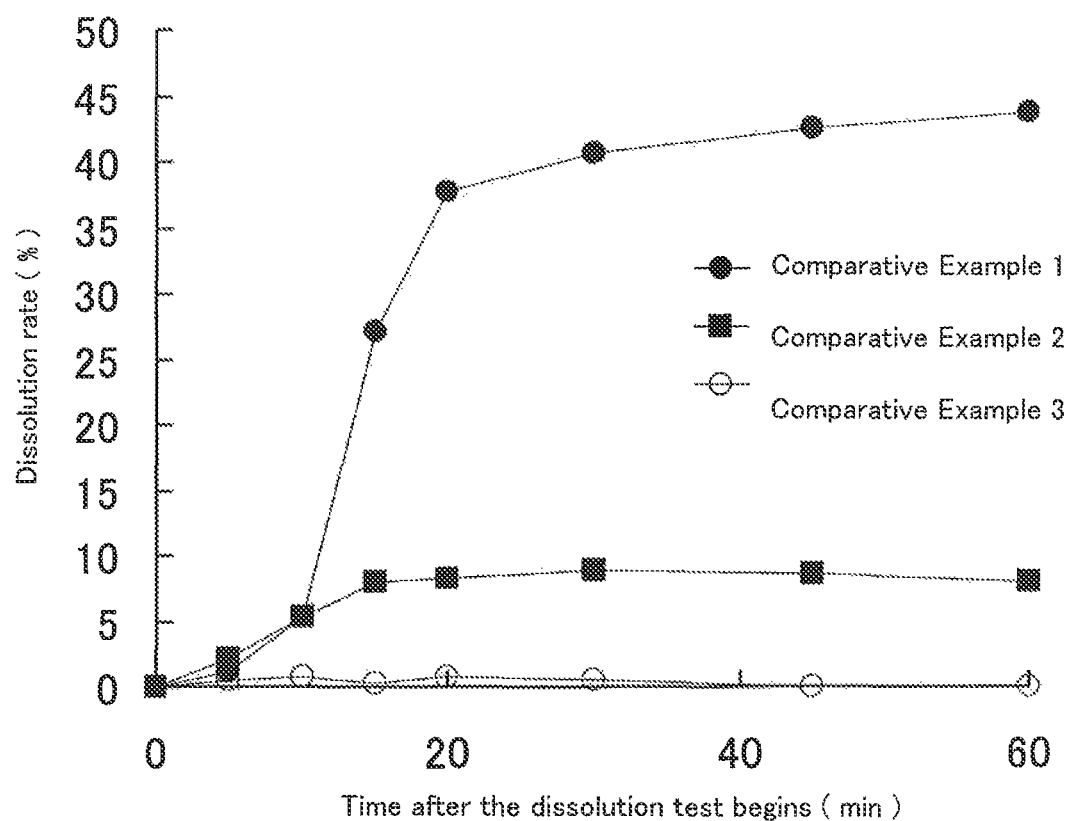
FIG. 1 shows the dissolving behavior of compound C-3B in the preparations of comparative examples 1 to 3. The vertical axis indicates the dissolving rate (%) of the drug and the horizontal axis indicates the time (minutes) elapsed after the dissolution test begins.

The terms used in this description are defined as follows.

"Poor solubility" means a state where the solubility in a solvent, especially water, a buffer solution, or a gastrointestinal tract inner liquid is 1 mg/ml or less, preferably 100 µg/ml or less, more preferably 10 µg/ml less, particularly preferably 1 µg/ml or less, and most preferably 0.1 µg/ml or less. It is preferably poorly soluble in any solvent with a pH of 7 or less, more preferably poorly soluble in any solvent with a pH of 4 to 7, even more preferably poorly soluble in a solvent with a pH of 4 and/or 7. However, in the case of a compound having a basic group in the molecule, it is preferably poorly soluble in any solvent with a pH of 7 or more, more preferably poorly soluble in any solvent with a pH of 7 to 9, even more preferably poorly soluble in a solvent with a pH of 7 and/or 9. The solvent to measure the solubility is not particularly limited, but a solvent with a pH of 4 includes, for example, an acetic acid buffer solution, citrate buffer solution and others. A solvent with a pH of 5 includes, for example, an acetic acid buffer solution, citrate buffer solution, phosphate buffer solution and others. A solvent with a pH of 7 includes, for example, water, a phosphate buffer and others. A solvent with a pH of 9 includes, for example, carbonic acid buffer solution and others. The temperature for measuring the solubility in each of the cases is preferably in the range of from 20 to 40° C., more preferably 37° C.

A "poorly soluble drug" may be one type, or two types or more of components selected from, among others, nutritious tonics, antipyretic painkilling antiphlogistic drugs (for example, nonsteroidal antiinflammatory drugs), psychotropic drugs, anti-anxiety drugs, antidepressants, sedative hypnotics, antispasmodic drugs, central nervous system acting drugs, brain metabolism improvement agents, cerebral circulation improvement agents, antiepileptics, sympathomimetic drugs, digestive medicines, antacid, antiulcer drugs, antitussive expectorant drugs, antiemetic drugs, respiratory accelerants, bronchodilators, antiallergic agents, dental buccals, antihistamines, cardiotonic drugs, antiarrhythmic agents, diuretics, antihypertensive drugs, vasoconstrictor drugs, coronary vasodilators, peripheral vasodilators, hyperlipidemic drugs, platelets production modifiers, choleretic drugs, antibiotics, chemotherapic drugs, diabetic drugs, antiosteoporosis drugs, antirheumatic drugs, skeletal muscle relaxants, antispasmodic agents, hormone drugs, alkaloidal narcotic drugs, sulfa drugs, gout suppressants, anticoagulants, anticancer drugs, bile acid.

A "poorly soluble drug having an acidic group in the molecule" means a compound having an acidic group in the molecule, its pharmaceutically acceptable salt or solvate thereof, but a compound having an acidic group in the molecule is preferable. The acidic group is preferably one or more selected from the group consisting of a carboxyl group, sulfo group, sulfino group, a phosphono group, and phenolic hydroxy group, more preferably a carboxyl group, a sulfo group, or a phenolic hydroxy group, and most preferably a carboxyl group. The acidic group preferably does not have a basic group in the molecule.

A "poorly soluble drug, having a basic group in the molecule" means a compound having a basic group in the molecule, its pharmaceutically acceptable salt or solvate thereof, but a compound having a basic group in the molecule is preferable. The basic group is preferably one or more selected from the group consisting of an amino group, an amidino group, a guanidino group, ammonium group, cyclic amino group, and a nucleic acid base. The basic group preferably does not have an acidic group in the molecule.

A poorly soluble drug having an acidic group in the molecule is preferably, among others, an optically active compound represented by Formula (I) disclosed in WO 2009/017098:

[Chemical formula 2]

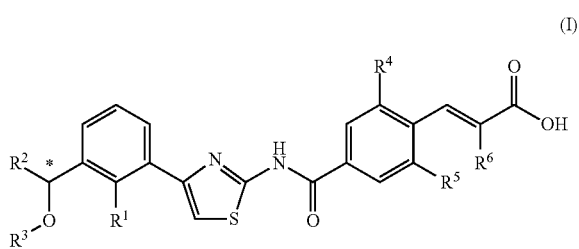

(I)

wherein, $R^1$ is a halogen atom or C1-C3 alkyl oxy; $R^2$ is C1-C8 alkyl; $R^3$ is C1-C8 alkyl; $R^4$ and $R^5$ are each independently a fluorine atom or a chlorine atom; $R^6$ is C1-C3 alkyl or C1-C3 alkyl oxy; and a carbon atom with a "*" attached to it is an asymmetric carbon;

its pharmaceutically acceptable salt, or solvate thereof.

A group of preferable substituents of R1 to R6 of a compound represented by Formula (I) are represented by (Ia) to (In). A compound of a possible combination of the substituents is preferable.

R1 is preferably (Ia) a halogen atom or C1-C3 alkyloxy, more preferably (Ib) a fluorine atom or methyloxy, and most preferably (Ic) methyloxy.

R2 is preferably (Id) C1-C8 alkyl, more preferably (Ie) C1-C6 alkyl.

R3 is preferably (I) C1-C8 alkyl, more preferably (Ig) C1-C6 alkyl.

R4 and R5 are the same, and are preferably (Ih) a fluorine atom or a chlorine atom, more preferably (Ii) a chlorine atom.

R6 is preferably (Ij) C1-C3 alkyl or C1-C3 alkyloxy, more preferably (Ik) C1-C3 alkyl, and most preferably (Il) methyl.

Optical rotation of an optical isomer is preferably (Im) (+) or (−), more preferably (In) (−).

As an optically active compound represented by Formula (I), any of the following optically active compounds is preferable.

[Chemical formula 3]

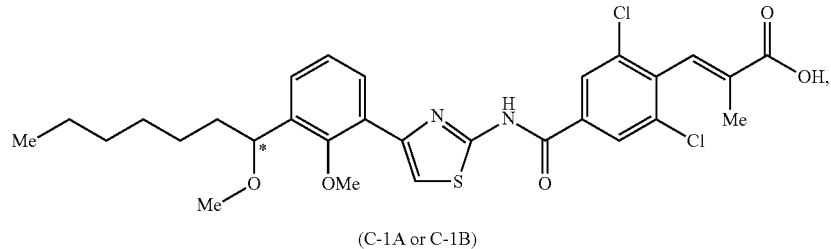

(C-1A or C-1B)

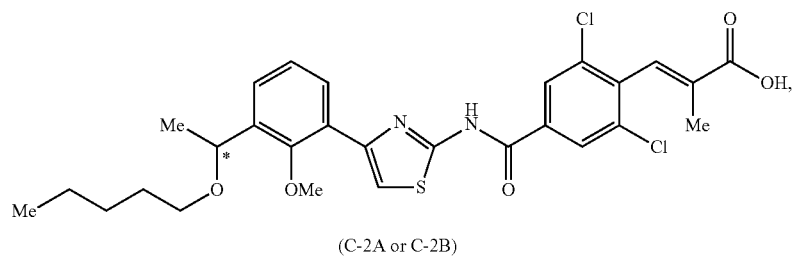

(C-2A or C-2B)

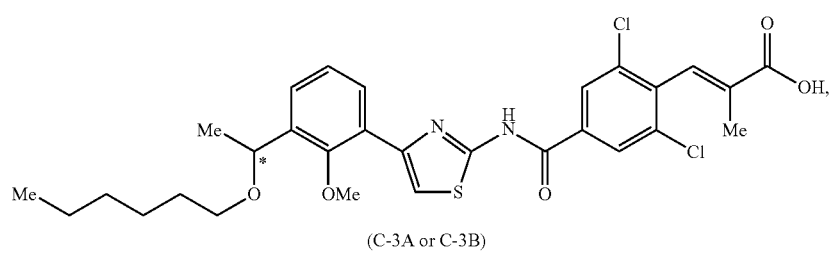

(C-3A or C-3B)

-continued
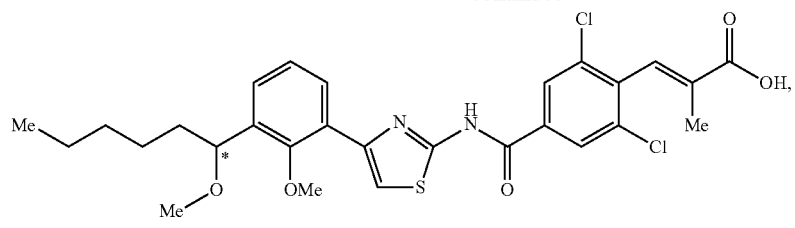
(C-4A or C-4B)
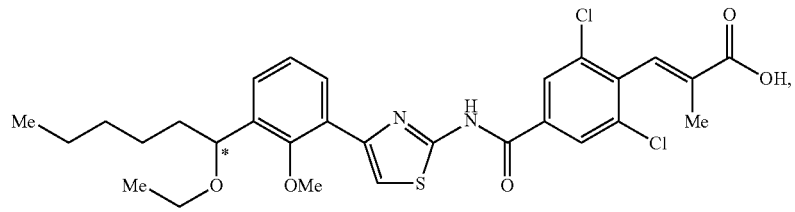
(C-5A or C-5B)
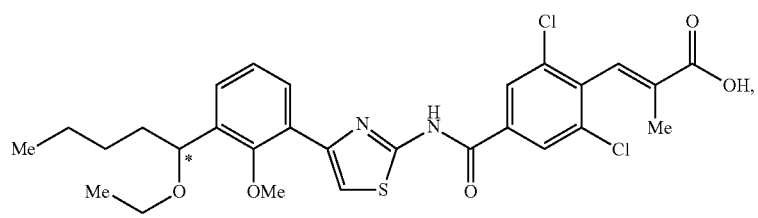
(C-6A or C-6B)
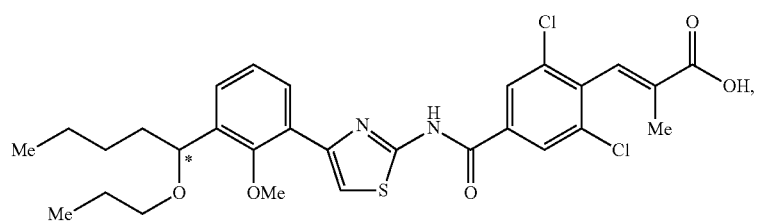
(C-7A or C-7B)
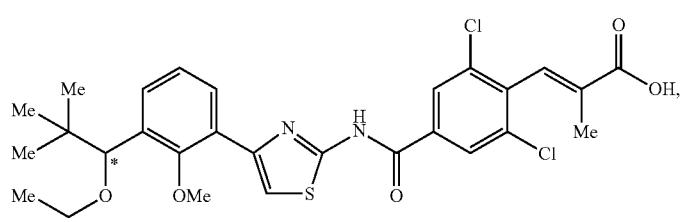
(C-8A or C-8B)
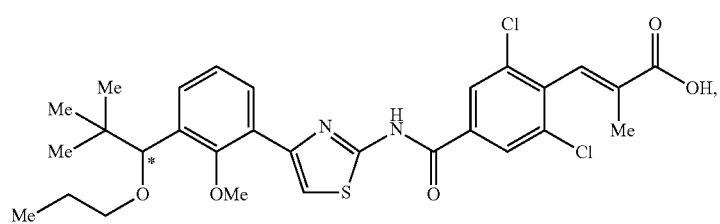
(C-9A or C-9B)

-continued
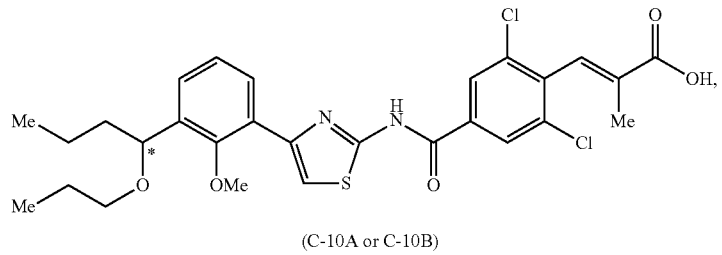
(C-10A or C-10B)
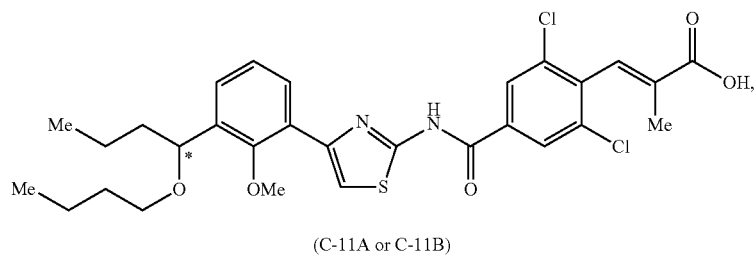
(C-11A or C-11B)
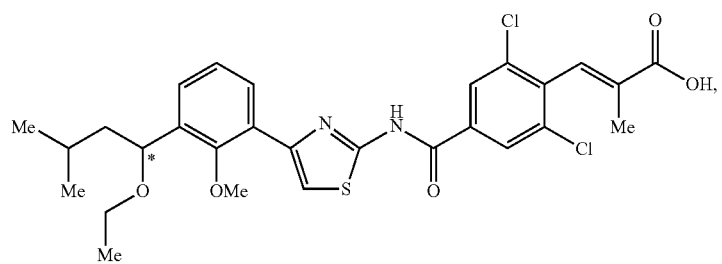
(C-12A or C-12B)
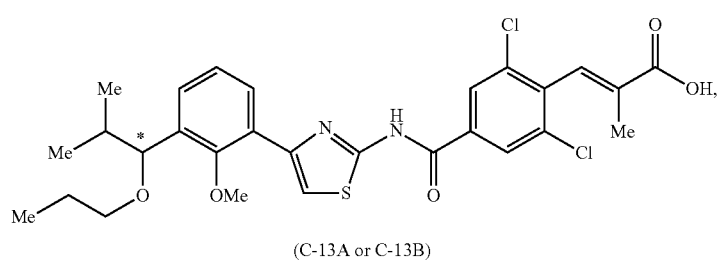
(C-13A or C-13B)
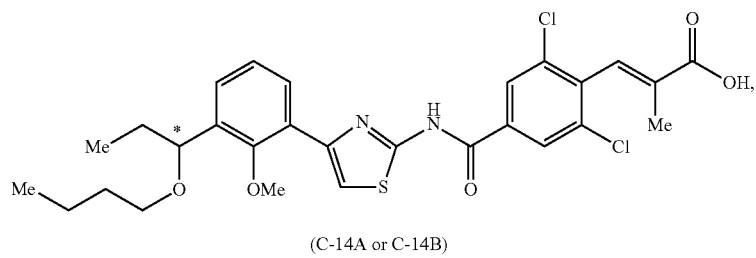
(C-14A or C-14B)
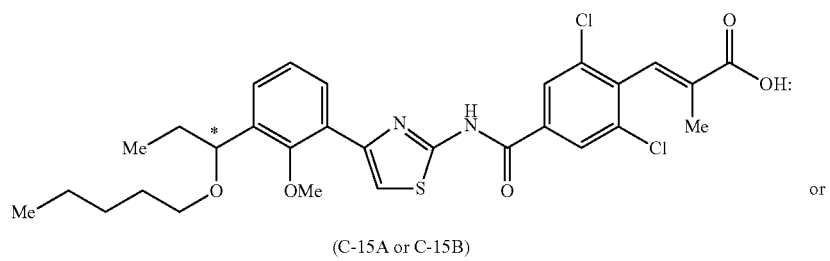
(C-15A or C-15B)
or

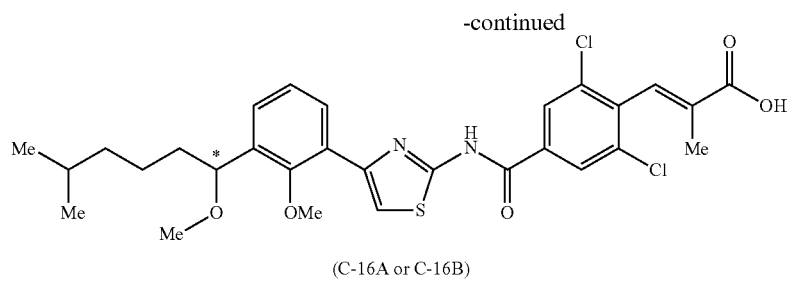

(C-16A or C-16B)

wherein Me represents a methyl; and carbon atom with "*" attached to it represents an asymmetric carbon. The optically active compound represented by Formula (I) is more preferably (E)-3-(2,6-dichloro-4-{4-[3-(1-hexyloxyethyl)-2-methyloxyphenyl]thiazole 2-yl carbamoyl}phenyl)-2-methylacrylic acid, and most preferably (S)-(E)-3-(2,6-dichloro-4-{4-[3-(1-hexyloxyethyl)-2-methyloxyphenyl]thiazole 2-yl carbamoyl}phenyl)-2-methylacrylic acid ("compound C-3B" described in WO 2009/017098). The solubility of compound C-3B in a solvent with a pH of 7 or less is 0.0004 μg/ml or less, and is a drug with extremely poor solubility of poorly soluble drugs.

Meanwhile, other preferable poorly soluble drugs having an acidic group in the molecule include, among others, a nonsteroidal antiinflammatory drug and a bile acid. Examples include indomerbacin, ketoprofen, flurbiprofen, loxoprofen, ketorolac, felbinac, difenac, salicylic acid, glycol salicylate, acetylsalicylic acid, flufenamic acid, mefenamic acid, acemetacin, alclofenac, ibuprofen, sulindac, tolmetin, lobenzarit, penicillamine, oxaprozin, diflunisal, fenbufen, fentiazac, naproxen, pranoprofen, tiaprofen, suprofen, oxaprozin, etodolac, zaltofen, telmisartan, ursodeoxycholic acid, or its pharmaceutically acceptable salt, and preferably indomethacin, ibuprofen, mefenamic acid, or ursodeoxycholic acid.

Examples of a poorly soluble drug having a basic group in the molecule include, among others, maprotiline hydrochloride, papaverine hydrochloride, norepinephrine, berberine chloride, Cetraxate hydrochloride, sulfamethoxazole, metronidazole, diazepam, cimetidine, famotidine, bromhexine hydrochloride, difenidol hydrochloride, caffeine, digoxin, verapamil hydrochloride, erythromycin, clarithromycin, kitasamycin, josamycin, roxithromycin, midecamycin.

A "halogen atom" means a fluorine atom, a chlorine atom, a bromine atom, or an iodine atom, and preferably a fluorine atom, a chlorine atom, or a bromine atom.

An "alkyl" includes a straight chain or a branched chain monovalent hydrocarbon group with a carbon number of 1 to 8. Examples include, among others, methyl, ethyl, n-propyl, isopropyl, n-buryl, isobutyl, sec-butyl, tert-butyl, n-pentyl, isopentyl, neo pentyl, n-hexyl, isohexyl, n-heptyl, n-octyl, preferably C1-C6 alkyl, and more preferably C1-C4 alkyl.

Examples of an "alkyloxy" include, among others, methyloxy, ethyloxy, propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hex yloxy, n-heptyloxy, n-octyloxy, preferably C1-C6 alkyloxy, and more preferably C1-C4 alkyloxy.

In the chemical formula stated above, carbon atom with "*" attached to it represents an asymmetric carbon. A compound with "*" attached to it represents that the absolute positioning of a carbon atom with "*" attached to it is a R-positioning or a S-positioning. For example, an optically active compound shown by formula (I) includes an optical isomer of R-positioning ((R)-I) or an optical isomer of S-positioning ((S)-I).

[Chemical formula 4]

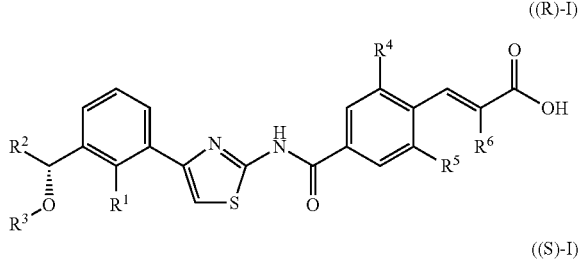

((R)-I)

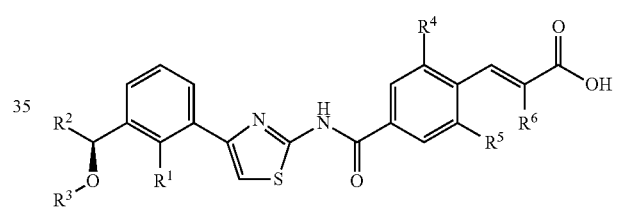

((S)-I)

A "poorly soluble drug" in the preparation of the present invention is preferably crystal. The crystalline state of a poorly soluble drug may be verified by solid state NMR or X-ray powder diffraction.

Content of a "poorly soluble drug" relative to the amount of the granulated substance of the present invention is preferably 0.1 to 20 weight %, more preferably 1 to 10 weight % and even more preferably 2 to 6 weight %.

An "alkaline agent" is not particularly limited as long as the pH of its 5 weight % aqueous solution or a suspension is preferably 9 or more, and it may be a mixture of two or more types. Moreover, one that has a small dissolution rate in water is preferable. Examples include ones containing in the molecule one or more atoms selected from the group consisting of magnesium, calcium and aluminum. Preferably, the examples include ore or more compounds selected from the group consisting of magnesium oxide, magnesium hydroxide, hydroxylation alumina magnesium, synthetic hydrotalcite, calcium carbonate, magnesium carbonate, or calcium silicate, and more preferably they include magnesium oxide, magnesium hydroxide or a mixture thereof.

By compounding an alkaline agent only inside the granulated substance containing a poorly soluble drug having an acidic group in the molecule, an alkali environment may be created only inside the granulated substance. As a result, an alkali environment may be created in the vicinity of a poorly soluble drug by compounding a small amount of alkaline agent and in an effective manner relative to the case where an alkali environment is created in the entire preparation.

Content of each of the alkaline agents relative to the amount of the granulated substance of the present invention is preferably 0.5 to 30 weight %, and more preferably 2 to 25 weight %.

The content of magnesium oxide relative to the amount of the granulated substance of the present invention is preferably 0.5 to 30 weight %, more preferably 2 to 25 weight %, and even more preferably 2.5 to 10 weight %. The content of magnesium hydroxide relative to the amount of the granulated substance of the present invention is preferably 0.5 to 30 weight %, more preferably 2 to 25 weight %, and even more preferably 5 to 20 weight %. The content of hydroxylation alumina magnesium relative to the amount of the granulated substance of the present invention is preferably 0.5 to 30 weight %, more preferably 2 to 25 weight %, and even more preferably 7.5 to 20 weight %. The content of synthetic hydrotalcite relative to the amount of the granulated substance of the present invention is preferably 0.5 to 30 weight %, more preferably 2 to 25 weight %, and even more preferably 5 to 20 weight %.

When the contents are more than those stated above, stability of some of the poorly soluble drugs may degrade, and the action of an additive, particularly of a disintegrator, may deteriorate over time. Alternatively, when the contents are less than those stated above, the vicinity of a poorly soluble drug in the granulated substance cannot be turned into a sufficiently alkali environment, and the solubility of the poorly soluble drug may not be improved.

An "acid" is not particularly limited as long as the pH of its 5 weight % aqueous solution or a suspension is preferably 5 or less, and it may be a mixture of two or more types. Examples include citric acid, citric acid, tartaric acid, succinic acid and others.

By compounding an acid only inside the granulated substance containing a poorly soluble drug having a basic group in the molecule, an acidic environment may be created only inside the granulated substance. As a result, an acidic environment may be created in the vicinity of a poorly soluble drug by compounding a small amount of acid and in an effective manner relative to the case where an acidic environment is created in the entire preparation.

A "surfactant" may be of any kind as long as it is pharmaceutically applicable, and it may be a mixture of two or more types. A surfactant may improve the solubility of a poorly soluble drug by improving the wettability of the poorly soluble drug. Either an ionic surfactant or a nonionic surfactant may be used, but an ionic surfactant is more preferable. The ionic surfactant is preferably one or more selected from the group consisting of sulfuric ester salt, carboxylate, and sulfonate, more preferably sulfuric ester salt, and most preferably sodium laurel sulfate. A nonionic surfactant is preferably sugar fatty acid ester and/or polyoxy alkylene glycol, more preferably sucrose fatty acid ester and/or polyoxyethylene polyoxypropylene glycol.

The content of the surfactant relative to the amount of the granulated substance of the present invention is preferably 0.2 to 50 weight %, and more preferably 1 to 40 weight %.

The content of sodium lauryl sulfate relative to the amount of the granulated substance of the present invention is preferably 0.2 to 50 weight %, more preferably 1 to 40 weight %, even more preferably 2.5 to 30 weight %.

When the contents are more than those stated above, the granulating property may degrade due to rise in viscosity. When the contents are less than those stated above, the wettability of the poorly soluble drug in the granulated substance may not be sufficiently improved and the solubility of the poorly soluble drug may not be improved.

A "binder" may be of any kind as long as it is pharmaceutically applicable, and it may be a mixture of two or more types. Specifically, examples include a cellulosic, polyvinyl pyrrolidone, hydroxypropyl starch, carboxymethyl starch sodium and others, and preferably a cellulosic and/or polyvinyl pyrrolidone.

Examples of a cellulosic; include hydroxypropylmethyl cellulose; a mixture of fumaric acid, stearic, acid, polyvinyl acetal diethylamino acetate and hydroxypropylmethyl cellulose; hydroxypropyl cellulose; carmellose; carmellose sodium; croscarmellose sodium; hydroxyethylmethyl cellulose; hydroxyethyl cellulose and others, preferably hydroxypropyl cellulose.

The content of the binder relative to the amount of the granulated substance of the present invention is 0.1 to 20 weight %, and preferably 0.5 to 10 weight %.

The content of hydroxypropyl cellulose relative to the amount of the granulated substance of the present invention is preferably 0.5 to 20 weight %, more preferably 0.5 to 10 weight %, and even more preferably 1 to 5 weight %.

When an ionic surfactant with high solubility in water (e.g., sodium lauryl sulfate) is used as a surfactant, it is desirable to reduce the dissolution rate of the ionic surfactant by using a cellulosic as a binder.

An "excipient" may be of any kind as long as it is pharmaceutically applicable, and it may be a mixture of two or more types. Specifically, either a water soluble excipient or a water insoluble excipient may be used. More specifically, examples of the water soluble excipient include grape sugar, fruit sugar, lactose, sucrose, D-mannitol, erythritol, maltitol, trehalose, sorbitol and others. Examples of the water insoluble excipient include corn starch, potato starch, wheat starch, rice starch, crystalline cellulose, silicic anhydride, hydrous silicon dioxide and others. Preferable examples are one or more selected from the group consisting of D-mannitol, corn starch and crystalline cellulose.

The content of the water soluble excipient relative to the amount of the solubility improving preparation of the present invention is preferably 9 weight % or more, more preferably 15 weight % or more, even more preferably 35 weight % or more, and most preferably 50 weight % or more, and 95 weight % or less, and preferably 90 weight % or less.

A "lubricant" may be of any kind as long as it is pharmaceutically applicable, and it may be a mixture of two or more types. Examples include sucrose fatty acid ester, talc, hydrous silicon dioxide, metal stearate and others. Preferable examples are magnesium stearate and/or talc.

The content of the lubricant relative to the amount of the solubility improving preparation of the present invention is preferably 0.1 to 10 weight %, and more preferably 0.5 to 2.5 weight %.

A "disintegrator" may be of any kind as long as it is pharmaceutically applicable, and it may be a mixture of two or more types, but preferably it does not contain ones that may be substantively used as an alkaline agent or a surfactant sodium hydrogencarbonate). Examples of the disintegrator include a cellulosic, corn starch, alpha starch, starch derivative, polyvinyl pyrrolidone derivative, powdered agar and others. Preferable examples are a cellulosic, polyvinyl pyrrolidone derivative and starch derivative. Examples of the cellulosic include a low substituted hydroxypropyl cellulose, carmellose, carmellose calcium, croscarmellose sodium and others. Preferable examples are a low substituted hydroxypropyl cellulose and carmellose calcium.

Examples of the polyvinyl pyrrolidone derivative include crospovidone and others, and preferably crospovidone. Examples of the starch derivative include carboxymethyl starch sodium and others, and preferably carboxymethyl starch sodium.

The content of the disintegrator relative to the amount of the solubility improving preparation of the present invention is preferably 0.2 to 30 weight %, and more preferably 1 to 20 weight %.

The content of the low substituted hydroxypropyl cellulose relative to the amount of the solubility improving preparation of the present invention is preferably 0.2 to 30 weight %, more preferably 2.5 to 20 weight %, and even more preferably 5 to 15 weight %. The content of the carmellose calcium relative to the amount of the solubility improving preparation of the present invention is preferably 0.2 to 30 weight %, more preferably 1 to 20 weight %, and even more preferably 2 to 10 weight %. The content of the carboxymethyl starch sodium relative to the amount of the solubility improving preparation of the present invention is preferably 0.2 to 30 weight %, more preferably 1 to 20 weight %, even more preferably 3 to 10 weight %, and most preferably 3 to 7 weight %. The content of the crospovidone relative to the amount of the solubility improving preparation of the present invention is preferably 0.2 to 30 weight %, more preferably 1 to 20 weight %, and even more preferably 2 to 10 weight %.

When the contents are more than those stated above, the amount of water incorporated inside around the disintegrator becomes insufficient, and the disintegration may be lowered. When the contents are less than those stated above, the disintegrating action may not be sufficiently exhibited.

A "granulated substance" means a substance produced by granulation. The method for production is not limited sometimes. Examples include powders, particles, granules, powdered drug and others.

A "solid preparation" is not particularly limited as long as the preparation is a solid, but preferably it is an oral medicine. The form of the preparation may be, for example, tablet, capsule, powder, granule, pill and others as described in the General Rules for Preparations in the Japanese Pharmacopoeia, but the form is preferably in tablet or capsule, and more preferably in tablet.

Feature of the granulated substance of the present invention is to contain a poorly soluble drug, an alkaline agent or an acid, and a surfactant. Additionally, a binder, an excipient, a lubricant and others may be contained where appropriate, but a disintegrator does not substantially contain. Here, "a disintegrator does not substantially contain" means either a disintegrator does not contain at all, or a disintegrator contains in a small amount such that the disintegrating action intrinsically exhibited by a disintegrator cannot be produced. Preferably, the content of the disintegrator relative to the amount of the granulated substance of the present invention is less than about 0.5 weight %, preferably less than about 0.05 weight %, even more preferably less than about 0.005 weight %, and preferably in particular none. When a certain amount or more of the disintegrator is contained inside the granulated substance, at the rime of disintegration followed by orally administering a preparation, the structure of the granulated substance heavily disintegrates and the alkaline agent and the surfactant disperse from the vicinity of the poorly soluble drug, and thus the environment adequate for dissolution of the poorly soluble drug is lost. A preferable form of the preparation may be in the form of granule or powder as described in the General Rules for Preparations in the Japanese Pharmacopoeia. The poorly soluble drug preferably exists in a crystalline state in the granulated substance of the present invention. The crystalline state of the poorly soluble drug may be verified by solid state NMR or X-ray powder diffraction.

The granulated substance of the present invention may be produced by a publicly known means. Specifically, the method for production comprises: mixing, where appropriate, binder, excipient, lubricant and others with a poorly soluble drug, alkaline agent or acid, and surfactant; and granulating the resulting mixture by wet granulation method, for example, extruding granulation method, a fluidized bed granulation method, an agitation granulation method, spray granulation method, oscillating granulation method, disintegrating granulation method and others, preferably agitation granulation method. Preferably, the method for production comprises mixing a poorly soluble drug, an alkaline agent, a surfactant, a binder, and an excipient, and granulating the mixture. The granulation process may be preferably conducted by adding a binder solution, preferably an aqueous solution containing 1 to 20 weight % of a binder, more preferably an aqueous solution containing 5 to 15 weight % of a binder. After granulation, the granulated substance is preferably dried and refined.

The solubility improving preparation of the present invention is a solid preparation with a feature of containing a granulated substance of the present invention and a disintegrator, and also with a feature of existing a disintegrator in the external of the granulated substance and substantially not containing a disintegrator in the granulated substance. The solubility improving preparation is produced by mixing the disintegrator with the granulated substance of the present invention.

The solubility improving preparation of the present invention has only to contain an alkaline agent or an acid in the granulated substance, thus the compounding amount of the alkaline agent or the acid may be reduced to a relatively small amount. Moreover, the solubility of the poorly soluble drug may be improved relative to the case where the alkaline agent or the acid exists only in the external of the granulated substance. In the solubility improving preparation of the present invention, the solubility of the poorly soluble drug may be further improved by containing the disintegrator substantively only in the external of the granulated substance. The solubility improving preparation of the present invention may additionally contain binder, excipient, lubricant and others depending on needs. The form of the preparation may be tablet, capsule, powder, granule, pill and others as described in the General Rules for Preparations in the Japanese Pharmacopoeia, but the form is preferably in tablet or capsule, and more preferably in tablet.

The solubility improving preparation of the present invention may be produced by a publicly known means. Specifically, the method for production comprises mixing a disintegrator, and, depending on needs, binder, excipient, lubricant and others with the granulated substance of the present invention, followed by, for example, tablet compressing, capsule filling, or granulation. Tablet compression may be conducted with a device for conducting external lubrication tablet compression, a single punch tablet machine, a rotary tablet machine and others. Granulation may be conducted by a wet granulation method, for example, an extruding granulation method, a fluidized bed granulation method, an agitation granulation method, a spray granulation method, an oscillating granulation method, a disintegrating granulation method and others. Preferably, production may be conducted by externally adding a disintegrator and a lubricant to the granulated substance of the present invention, further mixing an excipient to the resulting mixture depending on needs, followed by tablet compression in this case, the tablet compression pressure is preferably 3 to 20 kN, more preferably 4 to 15 kN, and the tablet diameter is preferably 6 to 10 mm.

In the solubility improving preparation of the poorly soluble drug having an acidic group in the molecule of the present invention, with a view to further improving the solubility of the poorly soluble drug, the contents of the alkaline agent, the surfactant, and the binder relative to the amount of the granulated substance stated above, and the content of the disintegrator relative to the amount of the solid preparation stated above may be preferably set as follows. For example, relative to the amount of the granulated substance stated above, one or more alkaline agents are contained in an amount of 0.5 to 30 weight % a surfactant is contained in an amount of 0.2 to 50 weight %, and/or a binder is contained in an amount of 0.1 to 20 weight %, and relative to the amount of the solid preparation stated above, a disintegrator is contained in an amount of 0.2 to 30 weight %. More preferably, relative to the amount of the granulated substance stated above, magnesium oxide is contained in an amount of 0.5 to 30 weight %, magnesium hydroxide is contained in an amount of 0.5 to 30 weight %, sodium lauryl, sulfate is contained in an amount of 0.2 to 50 weight %, and/or hydroxypropyl cellulose is contained in an amount of 0.1 to 20 weight %, and relative to the amount of the solid preparation stated above, carmellose calcium as a disintegrator is contained in an amount of 0.2 to 30 weight %. More preferably, the contents may be set as follows. Relative to the amount of the granulated substance stated above, magnesium oxide is contained in an amount of 2.5 to 10 weight %, magnesium hydroxide is contained in an amount of 5 to 20 weight %, sodium lauryl sulfate is contained in an amount of 2.5 to 30 weight %, and/or hydroxypropyl cellulose is contained in an amount of 1 to 5 weight %, and relative to the amount of the solid preparation stated above, carmellose calcium as a disintegrator is contained in an amount of 3 to 7 weight %.

The solubility improving, preparation of the present invention may be coated. Coating can be conducted by a publicly known means. Examples of the coating agent include polyvinyl alcohol; ethyl cellulose; carboxymethylethyl cellulose carmellose; carmellose sodium; hydroxyethyl cellulose; hydroxyethylmethyl cellulose; hydroxypropyl cellulose; hydroxypropylmethyl cellulose; PVA copolymer; ethyl acrylate methyl methacrylate copolymer dispersion liquid; amino alkyl methacrylate copolymer; Opadry; carnauba wax; carboxy vinyl polymer; dry methacrylic acid copolymer; dimethylaminoethyl methacrylate methyl methacrylate copolymer; stearyl alcohol; shellac; cetanol; hydroxypropylmethyl cellulose acetatesuccinate; hydroxypropylmethyl cellulose phthalate; a mixture of fumaric acid, stearic acid, polyvinyl acetal diethylamino acetate and hydroxypropylmethyl cellulose; polyvinyl acetal diethylamino acetate; poly-vinyl alcohol; methacrylic acid copolymer; 2-methyl-5-vinylpyridine methyl acrylate methacrylic acid copolymer and others, and preferably hydroxypropylmethyl cellulose.

The coating agent stated above may contain one or more colorants. Examples of the colorants include food colorings such as Food Red No. 3, Food Yellow No. 5, and Food Blue No. 1, titanium oxide, iron sesquioxide, brown iron oxide, black iron oxide, copper chlorophyll; sodium copper-chlorophyllin, riboflavin, green tea powder and others, preferably titanium oxide and/or iron sesquioxide. The colorants may also have a light shielding effect. Some types of poorly soluble drugs may disintegrate by a reaction with an alkaline agent (e.g., magnesium oxide) under light with a wave length in a specific range, for example 300 to 500 nm. The disintegration can be inhibited by compounding a colorant, preferably iron sesquioxide.

The solubility improving, preparation of the present invention improves the solubility by creating an environment adequate for dissolution in the vicinity of the poorly soluble drug. The solubility improving preparation of a poorly soluble drug having an acidic group in the molecule of the present invention also exhibits high solubility particularly under an acidic pH condition. Methods for measuring the solubility include, for example, the dissolution test of Method 2 (Paddle method) of the 14th edition of Japanese Pharmacopoeia Dissolution Test. The solvent used in the dissolution test is preferably the 2nd fluid of the Japanese Pharmacopoeia Disintegration Test. The dissolution rate of the solubility improving preparation of the present invention after 60 minutes the dissolution test begins is preferably 20% or more, more preferably 30% or more, and most preferably 35% or more. Moreover, the dissolution rate of the solubility improving preparation of the present invention after 60 minutes the dissolution test begins is preferably 4 times or more, more preferably 10 times or more, and most preferably 20 times or more as much as that of a poorly soluble drug or a mixture powder containing the poorly soluble drug. For example, a solubility improving preparation with a poorly soluble drug of (S)-(E)-3-(2,6-dichloro-4-{4-[3-(1-hexyloxyethyl)-2-methyloxyphenyl] thiazole 2-yl carbamoyl}phenyl)-2-methylacrylic acid, can improve the dissolution rate after 60 minutes the dissolution test begins more than 100 times as much as that of the mixture powder containing the poorly soluble drug.

Accordingly, the solubility improving preparation of the present invention improves the solubility in both the stomach and the upper portion of the small intestine because the solubility of the poorly soluble drug, is little affected by the pH condition in the gastrointestinal tract, and as a result, it is useful as a preparation with drastically improved oral absorption of poorly soluble drugs.

EXAMPLES

The present invention is described in detail below by the following examples and comparative examples, but they are not intended to limit the present invention.

The dissolution tests were conducted pursuant to Method 2 (Paddle method) of the 14th edition of Japanese Pharmacopoeia Dissolution Test, using 900 ml of the 2nd fluid of the Japanese Pharmacopoeia Disintegration Test, and under the condition of 50 rotations per minute at 37° C. Concentrations of drugs were measured by a HPLC method.

Test Example 1

Solubility Evaluation of Drugs

A solvent was added to a drug, and ultrasonic irradiation treatment was performed on the resulting solution. The solution was agitated for 3 hours at 37° C. After 3 hours, the sample was filtered with a 0.45 μm filter, and the concentration of the drug in the filtrate was measured by a HPLC method. The solvents used were 100 mM of a citrate buffer solution (pH 4), 100 mM of a phosphate buffer (pH 7) and 100 mM of carbonic acid buffer solution (pH 9). The outcomes are shown in Table 1.

As a result, it was confirmed that (S)-(E)-3-(2,6-dichloro-4-{4-[3-(1-hexyloxyethyl)-2-methyloxyphenyl]thiazole 2-yl carbamoyl}phenyl)-2-methylacrylic acid (Compound C-3B) described in WO 2009/017098 was poorly soluble in an acidic and a neutral solvents, and that indomethacin was poorly soluble in an acidic solvent.

TABLE 1

| Drugs | Solubility (µg/ml) | | |
|---|---|---|---|
| | pH 4 | pH 7 | pH 9 |
| Compound (C-3B) | ≤0.0004 | ≤0.0004 | 7.7 |
| Indomethacin | 0.5 | 25 | n.d. |

(Note: "n.d." means solubility was not measured.)

Test Example 2

Examination of the Preparation Formulation

Formulation of comparative examples 1 to 3 is given in Table 2. Formulation used were Compound C-3B as a poorly soluble drug, magnesium oxide (Kanto Chemical Co., Inc.) as an alkaline agent, sodium lauryl sulfate (Nacalai Tesque) as a surfactant, carmellose calcium (Nichirin Chemical Industries, Ltd.) as a disintegrator, D-mannitol (Mannitol-S, Towa Kasei, Ltd.) and corn starch (corn starch, Nihon Shokuhinn Kako Co., Ltd.) as excipients, and hydroxypropyl cellulose (HPCSL, Nippon Soda Co., Ltd.) as a binder.

Comparative Example 1

Compound C-3B, D-mannitol, corn starch, sodium lauryl sulfate, magnesium oxide, hydroxypropyl cellulose, and carmellose calcium were mixed in a bag. The resulting mixture powder was placed on a mortar, and kneaded with a muddler while an adequate amount of water was dropped therein, and agitation granulation was conducted. After granulation, the granulated substance was dried for 30 minutes at 60° C. with a vented dryer, screened with a 30 mesh metal mesh, and the resulting granulated substance was filled in No. 2 gelatin capsules.

Comparative Example 2

Compound C-3B, D-mannitol, corn starch, sodium lauryl sulfate, hydroxypropyl cellulose, and carmellose calcium were mixed in a bag. The resulting mixture powder was placed on a mortar, and kneaded with a muddler while an adequate amount of water was dropped in, and agitation granulation was conducted. Magnesium oxide was further added to the resulting granulated substance, mid was mixed in a bag. A secondary granulation was conducted on a mortar. After granulation, the granulated substance was dried for 30 minutes at 60° C. with a vented dryer, screened with a 30 mesh metal mesh, and the resulting granulated substance was filled in No. 2 gelatin capsules.

Comparative Example 3

Compound C-3B, D-mannitol, corn starch, sodium lauryl sulfate, magnesium oxide, and carmellose calcium were mixed in a bag. The resulting mixture powder was filled in No. 2 gelatin capsules.

TABLE 2

| | | Comparative Example 1 | Comparative Example 2 | Comparative Example 3 |
|---|---|---|---|---|
| Poorly Soluble Drug | Compound (C-3B) | 10.0 | 10.0 | 10.0 |
| Excipient | D-mannitol | 52.0 | 52.0 | 50.0 |
| Excipient | Corn Starch | 20.0 | 20.0 | 20.0 |
| Surfactant | Sodium Lauryl Sulfate | 50.0 | 50.0 | 50.0 |
| Alkaline Agent | Magnesium Oxide | 50.0 | 50.0 | 50.0 |
| Binder | Hydroxypropyl Cellulose | 4.0 | 4.0 | — |
| Disintegrator | Carmellose Calcium | 14.0 | 14.0 | — |
| Total Amont (mg) | | 200.0 | 200.0 | 180.0 |

The outcomes of the dissolution tests are shown in FIG. 1. The outcomes derived from the encapsulated substances were compared and it was found that in the case of a mixture powder comprising a poorly soluble drug, an alkaline agent, and a surfactant (Comparative Example 3), the dissolution rate after 60 minutes the test began was 0.1% or less and dissolution of the poorly soluble drug was hardly recognized. Whereas in the case of a granulated substance with the entire preparation components collectively granulated (Comparative Example 1), the dissolution rate after 60 minutes the test began was 44%, and the solubility of a poorly soluble drug drastically improved relative to that of Comparative Example 3. On the other hand, in the case of a granulated substance on which a secondary granulation was performed by adding an alkaline agent to a granulated substance comprising a poorly soluble drug and a surfactant (Comparative Example 2), the dissolution rate after 60 minutes the test began was 8%, and the extent of improvement to the solubility of a poorly soluble drug was less compared to that of Comparative Example 1.

Accordingly, it was found that, in order to improve the solubility of a poorly soluble drug, a method of placing an alkaline agent and a surfactant in the vicinity of the drug, as in the case of the granulated substance of Comparative Example 1, was effective.

Test Example 3

Examination of Methods for Adding Disintegrators

Formulations of Example 1 and Comparative Example 4 are given in Table 3. Formulations used were Compound C-3B as a poorly soluble drug, synthetic hydrotalcite (Arukamak, Kyowa Chemical Industry Co., Ltd.) as an alkaline agent, sodium lauryl sulfate (Nacalai Tesque) as a surfactant, low substituted hydroxypropyl cellulose (L-HPC31, Shinetsu Chemical Co., Ltd.) as a disintegrator, D-mannitol (Mannitol-S, Towa Kasei, Ltd.) and corn starch (corn starch, Nihon Shokuhinn Kako Co., Ltd.) as excipients, and hydroxypropyl cellulose (LPCSL, Nippon Soda Co., Ltd.) as a binder.

Example 1

Compound C-3B, D-mannitol, corn starch, sodium lauryl sulfate and synthetic hydrotalcite were mixed in a bag. The resulting mixture powder was placed on a mortar, and kneaded with a muddler while 10 weight % of hydroxypropyl cellulose aqueous solution was dropped in, and agitation granulation was conducted. After granulation, the granulated substance was dried for 30 minutes at 60° C. with a vented dryer, and was screened with a 20 mesh metal mesh. Low substituted hydroxypropyl cellulose was further added to the resulting granulated substance, and was mixed in a bag. The resulting mixture was compressed with an ABM100S type static compressor (Tokyo Koki Seizosho, Ltd.) at a compressing pressure of 5 to 15 kN, and tablets with a diameter of 7 mm and each weighing 200 mg were produced.

Comparative Example 4

Compound C-3B, D-mannitol, corn starch, sodium lauryl sulfate, synthetic hydrotalcite and low substituted hydroxypropyl cellulose were mixed in a bag. The resulting mixture powder was placed on a mortar, and kneaded with a muddler while 10 weight % of hydroxypropyl cellulose aqueous solution was dropped in, and agitation granulation was conducted. After granulation, the granulated substance was dried for 30 minutes at 60° C. with a vented dryer, and was screened with a 20 mesh metal mesh. The resulting mixture was compressed with an ABM100S type static compressor (Tokyo Koki Seizosho, Ltd.) at a compressing pressure of 5 to 15 kN, and tablets with a diameter of 7 mm and each weighing 200 mg were produced.

TABLE 3

| | | | Example 1 | Comparative Example 4 |
|---|---|---|---|---|
| Granulated Substance | Poorly Soluble Drug | Compound (C-3B) | 10.0 | 10.0 |
| | Excipient | D-mannitol | 52.0 | 52.0 |
| | Excipient | Corn Starch | 20.0 | 20.0 |
| | Surfactant | Sodium Lauryl Sulfate | 50.0 | 50.0 |
| | Alkaline Agent | Synthetic Hydrotalcite | 50.0 | 50.0 |
| | Binder | Hydroxypropyl Cellulose | 4.0 | 4.0 |
| | Disintegrator | Low Substituted Hydroxypropyl Cellulose | — | 14.0 |
| External Addition | Disintegrator | Low Substituted Hydroxypropyl Cellulose | 14.0 | — |
| | Total Amount (mg) | | 200.0 | 200.0 |

Figure 2:
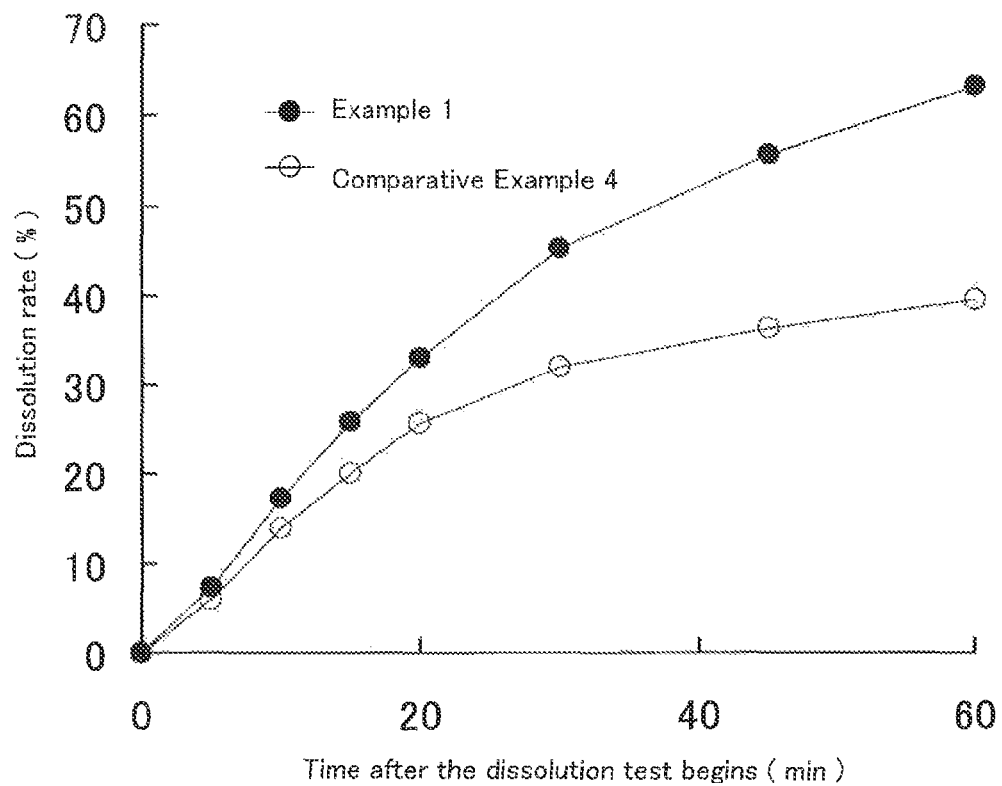
FIG. 2 shows the dissolving behavior of compound C-3B in the preparations of example 1 and comparative example 4. The vertical axis indicates the dissolving rate (%) of the drug and the horizontal axis indicates the time (minutes) elapsed after the dissolution test begins.

The outcomes of the dissolution tests are shown in FIG. 2. The preparation of the present invention provided in Example 1, which was prepared by externally adding a disintegrator to a granulated substance containing a poorly soluble drug, showed a dissolution rate after 60 minutes the test began of 63%, and the solubility of the poorly soluble drug exhibited a improvement compared to that of the granulated substance of Comparative Example 4 (having a dissolution rate after 60 minutes the test began of 40%), where the poorly soluble drug and the disintegrator were collectively granulated.

Test Example 4

Examination of Alkaline Agents

Formulations of Examples 2 to 6 are given in Table 4. Formulations used were Compound C-3B as a poorly soluble drug, synthetic hydrotalcite (Arukamak, Kyowa Chemical Industry Co., Ltd.), alumina magnesium hydroxide (Sanalmin, Kyowa Chemical Industry Co., Ltd.), magnesium hydroxide (Kyowasuimug, Kyowa Chemical Industry Co., Ltd.), magnesium oxide (Kanto Chemical Co., Ltd.), or calcium silicate (Flowlight R E, Tokuyama Corporation) as an alkaline agent, sodium lauryl sulfate (Emal O, Kao Corporation) as a surfactant, low substituted hydroxypropyl cellulose (L-HPC31, Shinetsu Chemical Co., Ltd.) as a disintegrator, D-mannitol (Mannitol-S, Towa Kasei, Ltd.) and corn starch (corn starch, Nihon Shokuhinn Kako Co., Ltd.) as excipients, hydroxypropyl cellulose (HPCSL, Nippon Soda Co., Ltd.) as a binder, and magnesium stearate (Taipei Chemical Industries Co., Ltd.) as a lubricant.

Examples 2 to 6

Compound C-3B, D-mannitol, corn starch, sodium lauryl sulfate and each of alkaline agents were mixed in a bag. The resulting mixture powder was placed on a mortar, and kneaded with a muddler while 10 weight % of hydroxypropyl cellulose aqueous solution was dropped in, and agitation granulation was conducted. After granulation, the granulated substance was dried for 30 minutes at 60° C. with a vented dryer, and was screened with a 20 mesh metal mesh. Low substituted hydroxypropyl cellulose and magnesium stearate were further added to the resulting granulated substance, and was mixed in a bag. The resulting mixture was compressed with an ABM100S type static compressor (Tokyo Koki Seizosho, Ltd.) at a compressing pressure of 10 kN, and tablets with a diameter of 7 mm and each weighing 200 mg were produced.

TABLE 4

| | | | Example 2 | Example 3 | Example 4 | Example 5 | Example 6 |
|---|---|---|---|---|---|---|---|
| Granulated Substance | Poorly Soluble Drug | Compound (C-3B) | 10.0 | 10.0 | 10.0 | 10.0 | 10.0 |
| | Excipient | D-mannitol | 50.0 | 41.4 | 48.0 | 59.2 | 18.0 |
| | Excipient | Corn Starch | 50.0 | 50.0 | 50.0 | 50.0 | 50.0 |
| | Binder | Hydroxypropyl Cellulose | 6.0 | 6.0 | 6.0 | 6.0 | 6.0 |
| | Surfactant | Sodium Lauryl Sulfate | 50.0 | 50.0 | 50.0 | 50.0 | 50.0 |
| | Alkaline Agent | Synthetic Hydrotalcite | 18.0 | — | — | — | — |
| | Alkaline Agent | Alumina Magnesium Hydroxide | — | 26.6 | — | — | — |
| | Alkaline Agent | Magnesium Hydroxide | — | — | 20.0 | — | — |
| | Alkaline Agent | Magnesium Oxide | — | — | — | 8.8 | — |
| | Alkaline Agent | Calcium Silicate | — | — | — | — | 50.0 |
| External Addition | Disintegrator | Low Substituted Hydroxypropyl Cellulose | 14.0 | 14.0 | 14.0 | 14.0 | 14.0 |
| | Lubricant | Magnesium Stearate | 2.0 | 2.0 | 2.0 | 2.0 | 2.0 |
| | Total Amount (mg) | | 200.0 | 200.0 | 200.0 | 200.0 | 200.0 |

Figure 3:
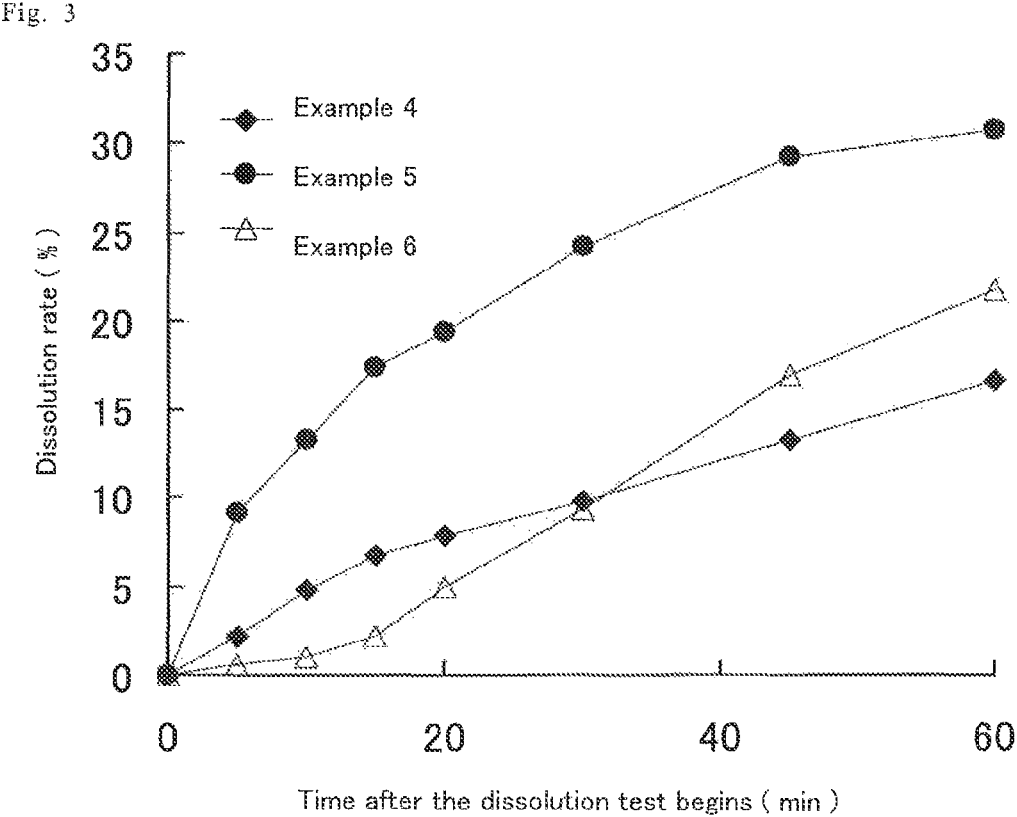
FIG. 3 shows the dissolving behavior of compound C-3B in the preparations of examples 4 to 6. The vertical axis indicates the dissolving rate (%) of the drug and the horizontal axis indicates the time (minutes) elapsed after the dissolution test begins.

The outcomes of the dissolution tests provided in Examples 4 to 6 are shown in FIG. 3. Each of the outcomes shows excellent dissolution rate.

Test Example 4

Dosage Dependency of Alkaline Agents

Formulations of Examples 7 to 10 and Comparative Example 5 are given in Table 5. Formulations used were Compound C-3B as a poorly soluble drug, magnesium oxide (Kanto Chemical Co., Ltd.), as an alkaline agent, sodium lauryl sulfate (Emal O, Kao Corporation) as a surfactant, low substituted hydroxypropyl cellulose (L-HPC31, Shinetsu Chemical Co., Ltd.) as a disintegrator, D-mannitol (Mannitol-S, Iowa Kasei, Ltd.) and corn starch (corn starch, Nihon Shokuhinn Kako Co., Ltd.) as excipients, hydroxypropyl cellulose (HPCSL, Nippon Soda Co., Ltd.) as a binder, and magnesium stearate (Taihei Chemical Industries Co., Ltd.) as a lubricant.

Examples 7 to 10 and Comparative Example 5

Compound C-3B, D-mannitol, corn starch, sodium lauryl sulfate and each of alkaline agents were mixed in a bag. The resulting mixture powder was placed on a mortar, and was kneaded with a muddler while 10 weight % of hydroxypropyl cellulose aqueous solution was dropped in, and agitation granulation was conducted. After granulation, the granulated substance was dried for 30 minutes at 60° C. with a vented dryer, and was screened with a 20 mesh metal mesh. Low substituted hydroxypropyl cellulose and magnesium stearate were further added to the resulting granulated substance, and was mixed in a bag. The resulting mixture was compressed with an ABM100S type static compressor (Tokyo Koki Seizosho, Ltd.) at a compressing pressure of 10 kN, and tablets with a diameter of 7 mm and each weighing 200 mg were produced.

Figure 4:
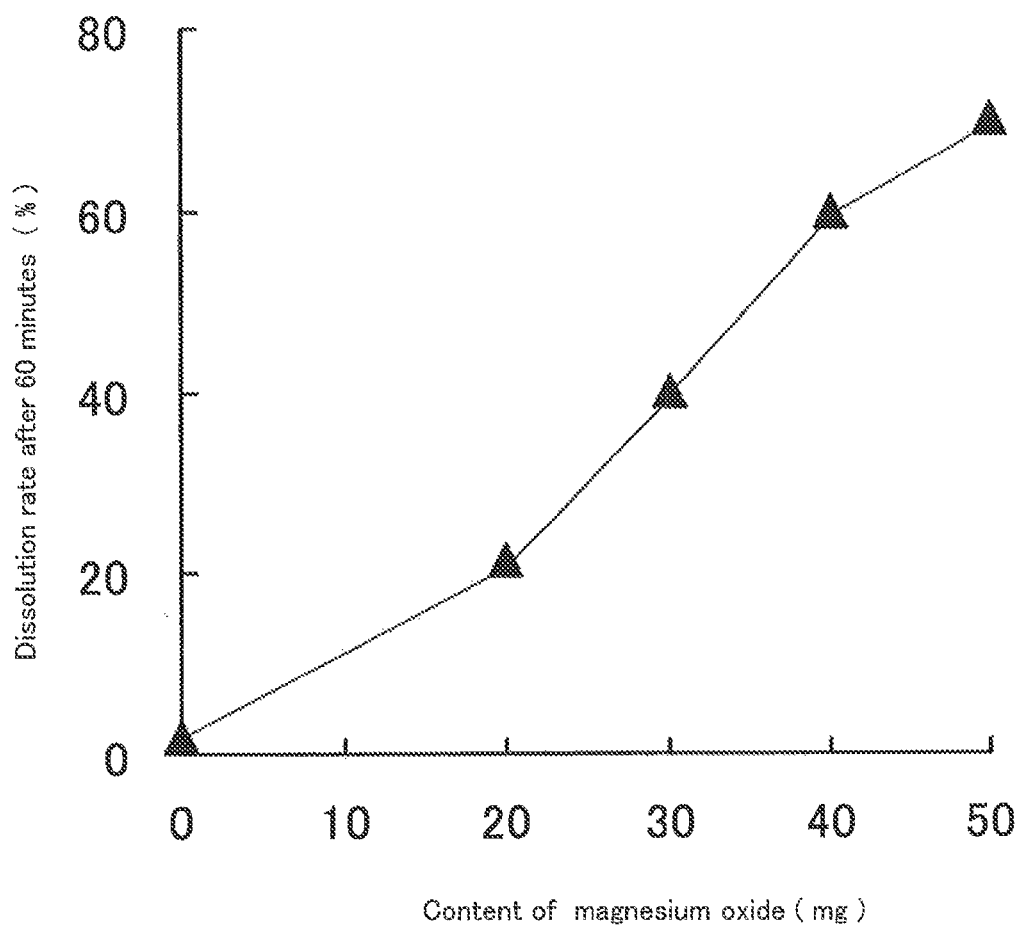
FIG. 4 shows the dosage dependency of the dissolution rate after 60 minutes the dissolution test begins on the magnesium oxide content of compound C-3B. The vertical axis indicates the dissolving rate (%) of the drug after 60 minutes the dissolution test begins and the horizontal axis indicates the magnesium oxide content (mg).

The outcomes of the dissolution tests are shown in FIG. 4. It was found that the dissolution rate of a poorly soluble drug depended on the content of magnesium oxide which is an alkaline agent.

Test Example 5

Examination of Surfactants

Formulations of Examples 11 to 14 are given in Table 6. Formulations used were Compound C-3B as a poorly soluble drug, magnesium hydroxide (Kyowasuimug. Kyowa Chemical Industry Co., Ltd.), magnesium oxide (Magnesium Oxide G, Kyowa Chemical Industry Co., Ltd.) and calcium silicate (Flowlight R E, Tokuyama Corporation) as alkaline agents, sodium lauryl sulfate (Emal O, Kao Corporation), sucrose fatty acid ester (Surfhope J-1616, Mitsubish Kagaku Foods Corporation), polyoxyethylene polyoxypropylene glycol (PEP101, Sanyo Chemical Industries, Ltd.) or polyoxyethylene (160) polyoxypropylene (30) glycol (Pronone #181 P, Nippon Oil and Fats Co., Ltd.) as a surfactant, carmellose calcium (Nichirin Chemical Industries, Ltd.) as a disintegrator, D-mannitol (Mannitol-S, Towa Kasei, Ltd.) as an excipient, hydroxypropyl cellulose (HPCSL, Nippon Soda Co., Ltd.) as a binder, and magnesium stearate (Taihei Chemical Industries Co., Ltd.) as a lubricant.

Examples 11 to 14

Compound C-3B, D-mannitol, calcium silicate, magnesium hydroxide, magnesium oxide, and each of surfactants were mixed in a bag. The resulting mixture powder was placed on a mortar, and kneaded with a muddler while 10 weight % of hydroxypropyl cellulose aqueous solution was dropped in, and agitation granulation was conducted. After granulation, the granulated substance was dried for 30 minutes at 60° C. with a vented dryer, and was screened with a 20 mesh metal mesh. Carmellose calcium and magnesium stearate were further added to the resulting granulated substance, and was mixed in a bag. The resulting mixture was compressed with an ABM100S type static compressor (Tokyo Koki Seizosho, Ltd.) at a compressing pressure of 10 kN, and tablets with a diameter of 7 mm and each weighing 200 mg were produced

TABLE 5

|  |  |  | Example 7 | Example 8 | Example 9 | Example 10 | Comparative Example 5 |
|---|---|---|---|---|---|---|---|
| Granulated Substance | Poorly Soluble Drug | Compound (C-3B) | 10.0 | 10.0 | 10.0 | 10.0 | 10.0 |
|  | Excipient | D-mannitol | 50.0 | 60.0 | 70.0 | 80.0 | 100.0 |
|  | Excipient | Corn Starch | 20.0 | 20.0 | 20.0 | 20.0 | 20.0 |
|  | Binder | Hydroxypropyl Cellulose | 4.0 | 4.0 | 4.0 | 4.0 | 4.0 |
|  | Surfactant | Sodium Lauryl Sulfate | 50.0 | 50.0 | 50.0 | 50.0 | 50.0 |
|  | Alkaline Agent | Magnesium Oxide | 50.0 | 40.0 | 30.0 | 20.0 | — |
| External Addition | Disintegrator | Low Substituted Hydroxypropyl Cellulose | 14.0 | 14.0 | 14.0 | 14.0 | 14.0 |
|  | Lubricant | Magnesium Stearate | 2.0 | 2.0 | 2.0 | 2.0 | 2.0 |
|  | Total Amount (mg) |  | 200.0 | 200.0 | 200.0 | 200.0 | 200.0 |

TABLE 6

|  |  |  | Example 11 | Example 12 | Example 13 | Example 14 |
|---|---|---|---|---|---|---|
| Granulated Substance | Poorly Soluble Drug | Compound (C-3B) | 10.0 | 10.0 | 10.0 | 10.0 |
|  | Excipient | D-mannitol | 39.2 | 39.2 | 39.2 | 39.2 |
|  | Binder | Hydroxypropyl Cellulose | 6.0 | 6.0 | 6.0 | 6.0 |
|  | Surfactant | Sodium Lauryl Sulfate | — | — | — | 50.0 |
|  | Surfactant | Sucrose fatty acid ester | 50.0 | — | — | — |
|  | Surfactant | Polyoxyethylene polyoxypropylene glycol | — | 50.0 | — | — |
|  | Surfactant | Polyoxyethylene (160) polyoxypropylene (30) glycol | — | — | 50.0 | — |
|  | Alkaline Agent | Magnesium Hydroxide | 20.0 | 20.0 | 20.0 | 20.0 |
|  | Alkaline Agent | Magnesium Oxide | 8.8 | 8.8 | 8.8 | 8.8 |
|  | Alkaline Agent | Calcium Silicate | 50.0 | 50.0 | 50.0 | 50.0 |
| Externa Addition | Disintegrator | Carmellose Calcium | 14.0 | 14.0 | 14.0 | 14.0 |
|  | Lubricant | Magnesium Strearate | 2.0 | 2.0 | 2.0 | 2.0 |
|  | Total Amount (mg) |  | 200.0 | 200.0 | 200.0 | 200.0 |

Figure 5:
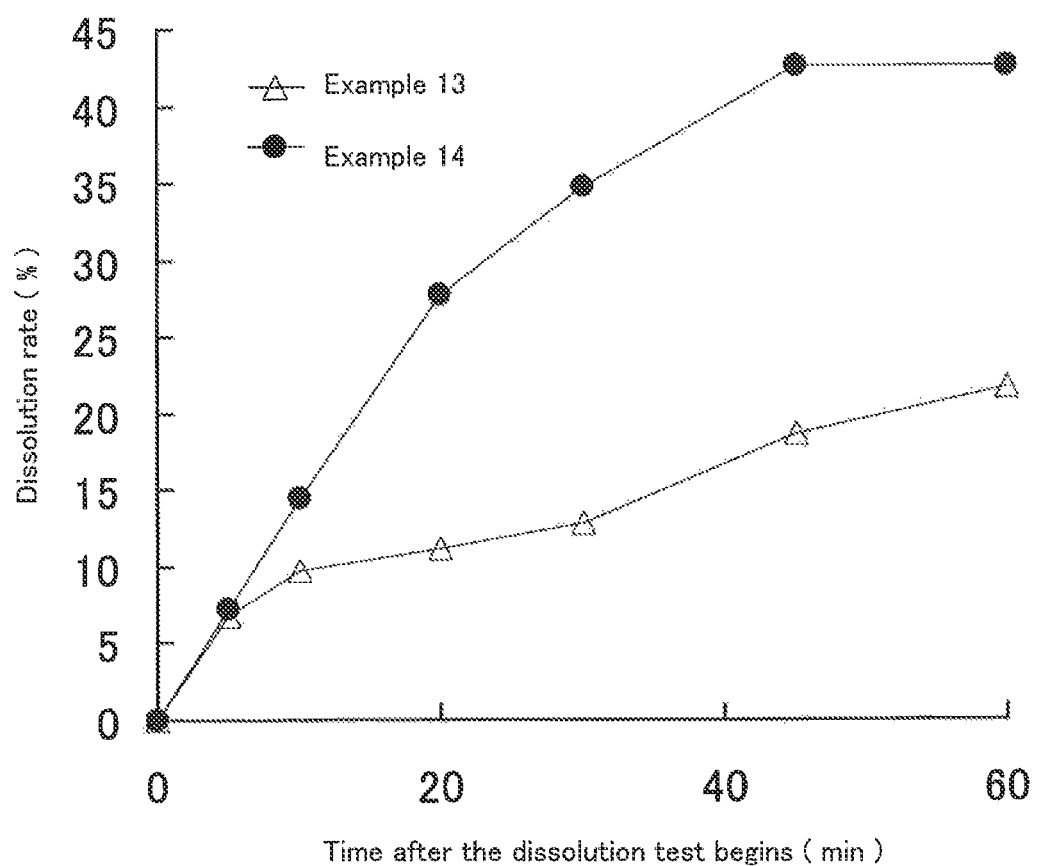
FIG. 5 shows the dissolving behavior of compound C-3B in the preparations of examples 13 and 14. The vertical axis indicates the dissolving rate (%) of the drug and the horizontal axis indicates the time (minutes) elapsed after the dissolution test begins.

The outcomes of the dissolution tests provided in Examples 13 to 14 are shown in FIG. 5. Each of the outcomes shows excellent dissolution rate.

Test Example 6

Dosage Dependency of Surfactants

Formulations of Examples 15 to 19 and Comparative Example 6 are given in Table 7. Formulations used were Compound C-31 as a poorly soluble drug, magnesium hydroxide (Kyowasuimug, Kyowa Chemical Industry Co., Ltd.), magnesium oxide (Magnesium Oxide G, Kyowa Chemical Industry Co., Ltd.) and calcium silicate (Flowlight R E, Tokuyama Corporation) as alkaline agents, sodium lauryl sulfate (Emal O, Kao Corporation), as a surfactant, carmellose, calcium (Nichirin Chemical Industries, Ltd.) as a disintegrator, D-mannitol (Mannitol-S, Towa Kasci, Ltd.) as an excipient, hydroxypropyl cellulose (HPCSL, Nippon Soda Co., Ltd.) as a binder, and magnesium stearate (Taihei Chemical Industries Co., Ltd.) as a lubricant.

Examples 15 to 19 and Comparative Example 6

Compound C-3B, D-mannitol, calcium silicate, magnesium hydroxide, magnesium oxide, and sodium lauryl sulfate were mixed in a bag. The resulting mixture powder was placed on a mortar, and kneaded with a muddler while 10 weight % of hydroxypropyl cellulose aqueous solution was dropped in, and agitation granulation was conducted. After granulation, the granulated substance was dried for 30 minutes at 60° C. with a vented dryer, and was screened with a 20 mesh metal mesh. Carmellose calcium and magnesium stearate were further added to the resulting granulated substance, and was mixed in a bag. The resulting mixture was compressed with an ABM100S type static compressor (Tokyo Koki Seizosho, Ltd.) at a compressing pressure of 10 kN, and tablets with a diameter of 7 mm and each weighing 200 mg were produced.

TABLE 7

|  |  |  | Example 15 | Example 16 | Example 17 | Example 18 | Example 19 | Comparative Example 6 |
|---|---|---|---|---|---|---|---|---|
| Granulated Substance | Poorly Soluble Drug | Compound (C-3B) | 10.0 | 10.0 | 10.0 | 10.0 | 10.0 | 10.0 |
|  | Excipient | D-mannitol | 79.2 | 99.2 | 109.2 | 114.2 | 119.2 | 129.2 |
|  | Binder | Hydroxypropyl Cellulose | 6.0 | 6.0 | 6.0 | 6.0 | 6.0 | 6.0 |
|  | Surfactant | Sodium Lauryl Sulfate | 50.0 | 30.0 | 20.0 | 15.0 | 10.0 | — |
|  | Alkaline Agent | Magnesium Hydroxide | 20.0 | 20.0 | 20.0 | 20.0 | 20.0 | 20.0 |
|  | Alkaline Agent | Magnesium Oxide | 8.8 | 8.8 | 8.8 | 8.8 | 8.8 | 8.8 |
|  | Alkaline Agent | Calcium Silicate | 10.0 | 10.0 | 10.0 | 10.0 | 10.0 | 10.0 |
| External Addition | Disintegrator | Carmellose Calcium | 14.0 | 14.0 | 14.0 | 14.0 | 14.0 | 14.0 |
|  | Lubricant | Magnesium Stearate | 2.0 | 2.0 | 2.0 | 2.0 | 2.0 | 2.0 |
|  | Total Amount (mg) |  | 200.0 | 200.0 | 200.0 | 200.0 | 200.0 | 200.0 |

Figure 6:
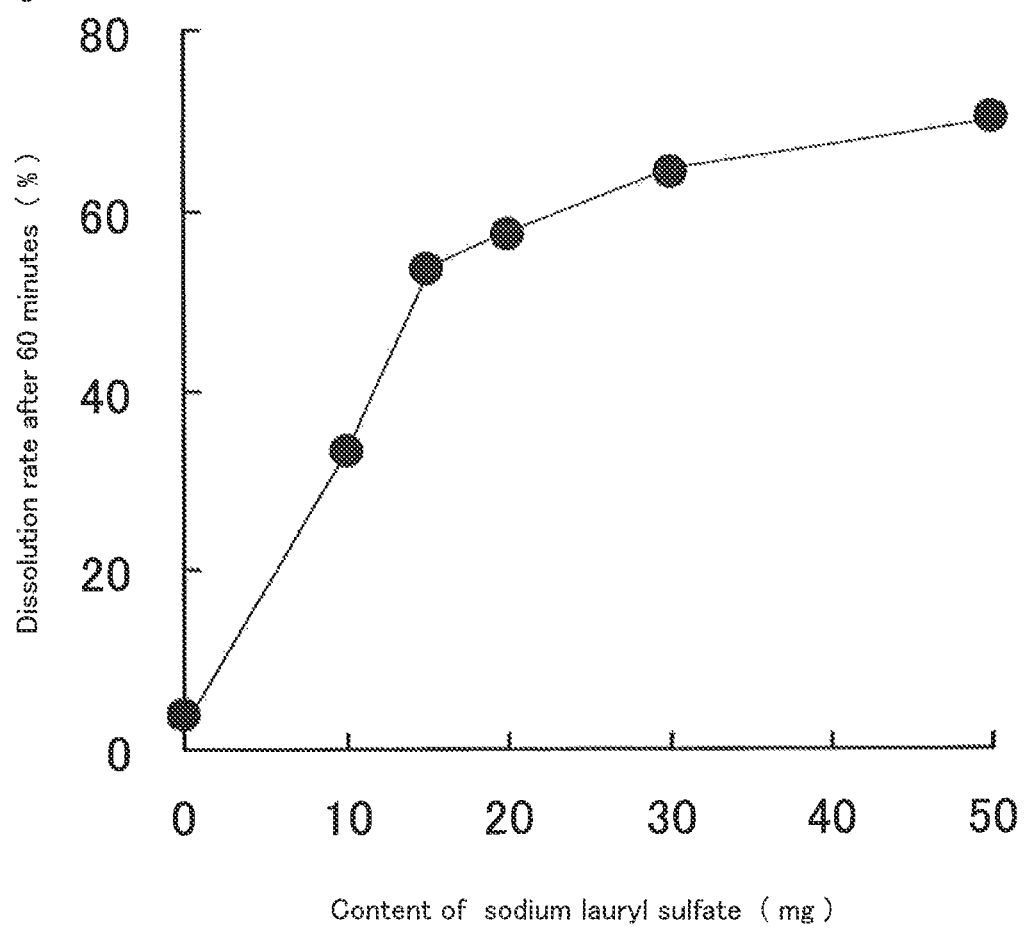
FIG. 6 shows the dosage dependency of the dissolution rate after 60 minutes the dissolution test begins on the sodium lauryl sulfate content of compound C-3B. The vertical axis indicates the dissolving rate (%) of the drug after 60 minutes the dissolution test begins and the horizontal axis indicates the sodium lauryl sulfate content (mg).

The outcomes of the dissolution tests are shown in FIG. 6. It was found that the dissolution rate of a poorly soluble drug depended on the content of sodium lauryl sulfate which is a surfactant.

Test Example 7

Oral Absorption Evaluation in Dogs

Formulation of Example 20 is given in Table 8. Formulations used were (S)-(E)-3-(2,6-dichloro-4-{4-[3-(1-hexyloxyethyl)-2-methyloxyphenyl]thiazole 2-yl carbamoyl}phenyl)-2-methylacrylic acid (Compound C-3B) described in WO 2009/017098 (Compound C-3B) as a poorly soluble drug, magnesium hydroxide (Kyowasuimug, Kyowa Chemical Industry Co., Ltd.) and magnesium oxide (Magnesium Oxide G, Kyowa Chemical Industry Co., Ltd.) as alkaline agents, sodium lauryl sulfate (Emal O, Kao Corporation) as a surfactant, carmellose calcium (Nichirin Chemical Industries, Ltd.) as a disintegrator, D-mannitol (Mannitol-5, Towa Kasei, Ltd.) and crystalline cellulose (Ceolus PH102, Asahi Kasei Corporation) as excipients, hydroxypropyl cellulose (HPCSL, Nippon Soda Co., Ltd.) as a binder, magnesium stearate (Taihei Chemical Industries Co., Ltd.) and talc (Fuji Talc Industrial Co., Ltd.) as lubricants, hydroxypropylmethyl cellulose (HPMC RW, Shinetsu Chemical Co., Ltd.) as a coating agent, triethyl citrate (Morimura Bros., Inc.) as a coating additive, and titanium oxide (Freund Corporation) as a coating colorant.

Example 20

Compound C-3B, magnesium lauryl sulfate, magnesium hydroxide, magnesium oxide, D-mannitol, and crystalline cellulose were placed in a 10-type high-speed mixer, and 7.7 weight % of hydroxypropyl cellulose aqueous solution was added thereto as a granulating liquid. Agitation granulation was conducted on the resulting mixture under the conditions of an agitation rotation rate of 200 rpm, a chopper rotation rate of 2000 rpm and a liquid velocity of 80 g/min. After granulation, the granulated substance was dried at 70° C., with a WSG 2&5 type fluid bed granulator, and the granulated substance was refined with a P-3 type power mill using a 24 mesh basket under the condition of a rotation rate of 3000 rpm. Carmellose calcium and magnesium stearate were further mixed with the resulting granulated substance. The resulting mixture was compressed with a RTM-S30K-2S type compressor at a compressing pressure of 10 kN. Tablets thus prepared were coated with a coating liquid containing hydroxypropyl cellulose, titanium oxide, triethyl citrate, and talc, using a HCT 48 type high coater under the conditions of a liquid spray pressure of 0.15 MPa and an air flow volume of 400 Pa. Coated tablets with a diameter of 7.5 mm were produced. A dissolution test was conducted on the coated tablets and it was found that the dissolution rate after 60 minutes the test began was 61%.

TABLE 8

| | | Example 20 |
|---|---|---|
| Granulated Substance | Compound (C-3B) | 10.00 |
| | Sodium Lauryl Sulfate | 20.00 |
| | Magnesium Hydroxidze | 20.00 |
| | Magnesium Oxide | 8.80 |
| | Hydroxypropyl Cellulose | 3.00 |
| | D-mannitol | 88.20 |
| | Crystalline cellulose | 40.00 |
| External Addition | Carmellose Calcium | 8.00 |
| | Magnesium Stearate | 2.00 |
| Coating | Hydroxypropylmethyl cellulose | 15.60 |
| | Titanium oxide | 4.80 |
| | Triethyl citrate | 1.80 |
| | Talc | 1.80 |
| | Total Amount (mg) | 224.00 |

Comparative Example 7

10 mg of compound C-3B and 50 mg of hydroxypropyl cellulose were mixed, and a suspension was prepared by suspending the resulting mixture in 10 ml of water.

Oral absorption in dogs was evaluated for the tablets prepared in Example 20 and the suspension prepared in Comparative Example 7, A male Beagle dog was fasted for 24 hours in advance and 1 tablet of a sample was orally administered. Blood was collected from the vein of the front limb before administration and a given time after administration, and the drug concentration in the plasma was measured with LC/MS/MS. The maximum drug concentration in the plasma (Cmax) and the time elapsed to attain the maximum drug concentration in the plasma (Tmax) were obtained, and the area under the drug concentration in the plasma-time curve (AUC) from the time of administration till 24 hours thereafter was calculated by the trapezoidal method.

Figure 7:
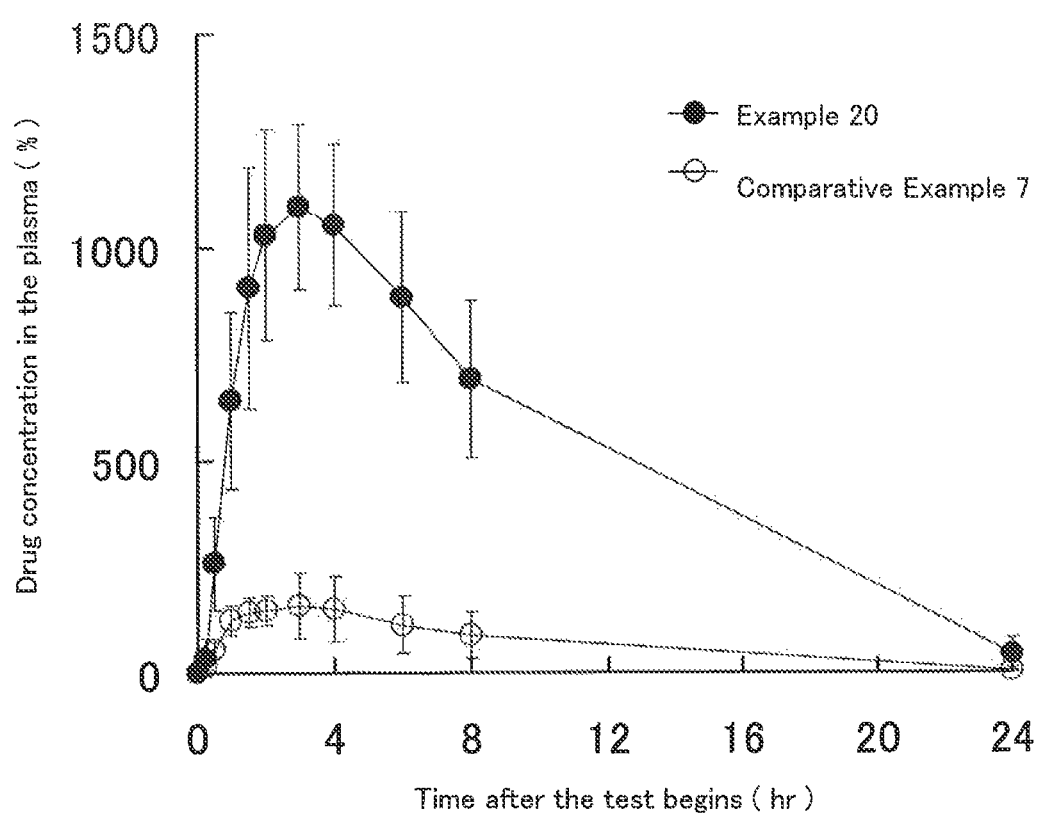
FIG. 7 shows the change in the drug concentration of compound C-3B in the plasma of a beagle dog triggered by oral administrations of preparations of example 20 and comparative example 7. The vertical axis indicates the drug concentration in the plasma (ng/ml) and the horizontal axis indicates the time (hours) elapsed after the dissolution test begins.

The outcome of the change in the drug concentration of compound C-3B in the plasma is shown in FIG. 7, and the outcomes of Tmax, Cmax and AUC values are shown in Table 9. The tablets provided in Example 20 comprising a granulated substance containing a poorly soluble drug, a surfactant and an alkaline agent, and a disintegrator exhibited an improvement in oral absorption of about eight times as much as that shown in the suspension provided in Comparative Example 7.

TABLE 9

| | Example 20 | Comparative Example 7 |
|---|---|---|
| Tmax (hour) | 3.3 ± 0.5 | 2.3 ± 0.5 |
| Cmax (ng/ml) | 1100 ± 200 | 170 ± 70 |
| AUC (ng · hour/ml) | 13000 ± 3000 | 1700 ± 900 |

Test Example 8

Production of a Solubility Improving Preparation

Formulations of Examples 20 to 2.3 are given in Table 10. Formulations used were (S)-(E)-3-(2,6-dichloro-4-{4-[3-(1-hexyloxyethyl)-2-methyloxyphenyl]thiazole 2-yl carbamoyl}phenyl)-2-methylacrylic acid described in WO 2009/017098 (Compound C-3B) as a poorly soluble drug, magnesium hydroxide (Kyowasuimug, Kyowa Chemical Industry Co., Ltd.) and magnesium oxide (Magnesium Oxide G, Kyowa Chemical Industry Co., Ltd.) as alkaline agents, sodium lauryl sulfate (Emal O, Kao Corporation) as a surfactant, carmellose calcium (Nichirin Chemical Industries, Ltd.) as a disintegrator, D-mannitol (Mannitol-S, Towa Kasei, Ltd.) and crystalline cellulose (Ceolus PH102, Asahi Kasei Corporation) as excipients, hydroxypropyl cellulose (HPCSL, Nippon Soda Co., Ltd.) as a binder, magnesium stearate (Taihei Chemical Industries Co., Ltd.) and talc (Fuji Talc Industrial Co., Ltd.) as lubricants, hydroxypropylmethyl cellulose (HPMC RW, Shinetsu Chemical Co., Ltd.) as a coating agent, triethyl citrate (Morimura Bros., Inc.) as a coating additive, and titanium oxide (Freund Corporation) and iron sesquioxide (Kishi Kasei Co., Ltd.) as coating colorants.

Examples 21 to 23

Compound C-3B, magnesium lauryl sulfate, magnesium hydroxide, magnesium oxide, D-mannitol, and crystalline cellulose were placed in a 10-type high-speed mixer, and 7.7 weight % of hydroxypropyl cellulose aqueous solution was added thereto as a granulating liquid. Agitation granulation was conducted on the resulting mixture under the conditions of an agitation rotation rate of 200 rpm, a chopper rotation rate of 2000 rpm and a liquid velocity of 80 g/min. After granulation, the granulated substance was dried at 70° C.

with a WSG 2&5 type fluid bed granulator, and the granulated substance was refined with a P-3 type power mill using a 24 mesh basket under the condition of a rotation rate of 3000 rpm. Carmellose calcium and magnesium stearate were further mixed with the resulting granulated substance. The resulting mixture was compressed with a RTM-S30K-2S type compressor at a compressing pressure of 10 kN. Tablets thus prepared were coated with a coating liquid containing hydroxypropyl cellulose, titanium oxide, iron sesquioxide, triethyl citrate, and talc, using a HCT 48 type high coater under the conditions of a liquid spray pressure of 0.15 MPa and an air flow volume of 400 Pa. Coated tablets with a diameter of 6 rum (Examples 21 and 23) or with a diameter of 10 mm (Example 22) were produced. Dissolution tests were conducted on the coated tablets and it was found that the dissolution rates after 60 minutes the test began were 52% (Example 21), 62% (Example 22) and 38% (Example 23).

TABLE 10

|  |  | Example 20 | Example 21 | Example 22 | Example 23 |
|---|---|---|---|---|---|
| Granulated Substance | Compound (C-3B) | 10.00 | 2.00 | 25.00 | 0.25 |
|  | Sodium Lauryl Sulfate | 20.00 | 10.00 | 50.00 | 0.50 |
|  | Magnesium Hydroxide | 20.00 | 10.00 | 50.00 | 1.25 |
|  | Magnesium Oxide | 8.80 | 4.40 | 22.00 | 0.55 |
|  | Hydroxypropyl Cellulose | 3.00 | 1.50 | 7.50 | 0.1875 |
|  | D-mannitol | 88.20 | 47.10 | 220.50 | 6.6375 |
|  | Crystalline cellulose | 40.00 | 20.00 | 100.00 | 2.50 |
| External Addition | Carmellose Calcium | 8.00 | 4.00 | 20.00 | 4.00 |
|  | Magnesium Stearate | 2.00 | 1.00 | 5.00 | 1.00 |
|  | D-mannitol | — | — | — | 83.125 |
| Coating | Hydroxypropylmethyl cellulose | 15.60 | 9.75 | 29.30 | 3.25 |
|  | Titanium oxide | 4.80 | 3.00 | 9.00 | 0.95 |
|  | Iron Sesquioxide | — | — | — | 0.05 |
|  | Triethyl citrate | 1.80 | 1.125 | 3.40 | 0.375 |
|  | Talc | 1.80 | 1.125 | 3.40 | 0.375 |
|  | Total Amount (mg) | 224.00 | 115.00 | 545.00 | 105.00 |

Oral absorption in dogs was evaluated for the tablets prepared in Examples 20 to 22 in a similar method as that of Test Example 7. The outcomes of Tmax, Cmax and ABC values are shown in Table 11. It was found that each of the tablets had a solubility improving ability of a poorly soluble drug.

TABLE 11

|  | Example 20 | Example 22 |
|---|---|---|
| Tmax (hour) | 3.3 ± 0.5 | 2.8 ± 1.1 |
| Cmax (ng/ml) | 1100 ± 200 | 2600 ± 600 |
| AUC (ng · hour/ml) | 13000 ± 3000 | 30000 ± 9000 |

Test Example 9

Solubility Improving Preparation of Indomethacin

Formulations of Example 24, Comparative Example 8 and Comparative Example 9 are given in Table 12. Formulations used were indomethacin (Kongo Chemical Co., Ltd.) as a poorly soluble drug, magnesium oxide (Kyowa. Chemical Industry Co., Ltd.) as an alkaline agent, sodium lauryl sulfate (Emal O, Kao Corporation) as a surfactant, carboxymethyl starch sodium (EXPLOTAB, Kimura Sangyo Co., Ltd.) as a disintegrator, D-mannitol (Rocket Co., Ltd.) and crystalline cellulose (Ceolus PH102, Asahi Kasei Corporation) as excipients, hydroxypropyl cellulose (HPCSL, Nippon Soda Co., Ltd.) as a binder, and magnesium stearate (Taihei Chemical Industries Co., Ltd.) as a lubricant.

Example 24

Indomethacin, D-mannitol, crystalline cellulose, hydroxypropyl cellulose, sodium lauryl sulfate, sucrose fatty acid ester, and magnesium oxide were mixed. The resulting mixture powder was placed on a mortar, and kneaded with a muddler while water was dropped in, and granulation was conducted. After granulation, the granulated substance was dried for 90 minutes at 50° C. with a VOS-30SD type vacuum dryer (EYELA), and was screened with a 30 mesh metal mesh. Carboxymethyl starch sodium and magnesium stearate were further added to the resulting granulated substance, and was mixed in a bag. The resulting mixture was compressed with an ABM100S type static compressor (Tokyo Koki Seizosho, Ltd.) at a compressing pressure of 4 kN, and tablets with a diameter of 7 mm and each weighing 200 mg were produced.

Comparative Example 8

Indomethacin, D-mannitol, crystalline cellulose, hydroxypropyl cellulose, sodium lauryl sulfate, sucrose fatty acid ester, magnesium oxide and carboxymethyl starch sodium were mixed. The resulting mixture powder was placed on a mortar, and kneaded with a muddler while water was dropped in, and granulation was conducted. After granulation, the granulated substance was dried for 90 minutes at 50° C. with a VOS-301SD type vacuum dryer (EVELA), and was screened with a 30 mesh metal mesh. Magnesium stearate was further added to the resulting granulated substance, and was mixed in a hag. The resulting mixture was compressed with an ABM100S type static compressor (Tokyo Koki Seizosho, Ltd.) at a compressing pressure of 4 kN, and tablets with a diameter of 7 ram and each weighing 200 mg were produced.

Comparative Example 9

Indomethacin, D-mannitol, crystalline cellulose, hydroxypropyl cellulose, sodium lauryl sulfate, sucrose fatty acid ester, magnesium oxide, carboxymethyl starch sodium, and magnesium stearate were mixed on a mortar, and a mixture powder was prepared.

TABLE 12

|  |  | Example 24 | Comparative Example 8 | Comparative Example 9 (Mixture Powder) |
|---|---|---|---|---|
| Poorly Soluble Drug | Indomethacin | 25.0 | 25.0 | 25.0 |
| Alkaline Agent | Magnesium Oxide | 40.0 | 40.0 | 40.0 |
| Surfactant | Sodium Lauryl Sulfate | 40.0 | 40.0 | 40.0 |
| Excipient | D-mannitol | 37.0 | 37.0 | 37.0 |
| Excipient | Crystalline cellulose | 50.0 | 50.0 | 50.0 |
| Binder | Hydroxypropyl Cellulose | 3.0 | 3.0 | 3.0 |
| Disintegrator | Carboxymethyl Starch Sodium | 12.0 | 12.0 (External Addition) | 12.0 |
| Lubricant | Magnesium Stearate | 1.0 | 1.0 | 1.0 |
|  | Total Amount (mg) | 200.0 | 200.0 | 200.0 |

Dissolution tests were conducted by replacing the 2nd fluid of the Japanese Pharmacopoeia Disintegration Test with an acetic acid buffer solution (with a pH of 4). Outcomes of the dissolution tests showed that the dissolution rates of the preparations of Example 24 and Comparative Example 9 after 60 minutes the test began were 42% and 10% respectively. It was found that, although indomethacin was intrinsically poorly soluble in acid, by making it into the solubility improving tablet of the present invention, solubility in an acidic solution could be improved.

Test Example 10

Solubility Improving Preparation of Ibuprofen, Mefenamic Acid, and Ursodeoxycholic Acid Formulations of Examples 25 to 27 and Comparative Examples 10 to 12 are given in Table 13. Formulations used were ibuprofen (Wake Pure Chemicals Indusrties, Ltd.), mefenamic acid (Wako Pure Chemicals Industries. Ltd.), or ursodeoxycholic acid (Wako Pure Chemicals Indusrties, Ltd.) as a poorly soluble drug, magnesium hydroxide (Kyowa Chemical Industry Co., Ltd.) and magnesium oxide (Kyowa Chemical Industry Co., Ltd.) as alkaline agents, sodium lauryl sulfate (Kao Corporation) as a surfactant, crospovidone (BASF) or carmellose calcium (Nichirin Chemical Industries, Ltd.) as a disintegrator, D-mannitol (Rocket. Co., Ltd.) and crystalline cellulose (Asahi Kasei Corporation) as excipients, hydroxypropyl cellulose (HPCSL, Nippon Soda Co., Ltd.) as a binder, and magnesium stearate (Taipei Chemical Industries Co., Ltd.) as a lubricant.

Examples 25 to 27

Each poorly soluble drug, magnesium hydroxide, magnesium, sodium lauryl sulfate, and D-mannitol were mixed. While 7.5 weight % of hydroxypropyl cellulose aqueous solution was dropped into the resulting mixture powder, granulation was conducted with an IMC-1855 type micro agitation granulating device (Imoto Machinery Co., Ltd.). After granulation, the granulated substance was dried for 30 minutes at 60° C. with a vented dryer (Satake Chemical Equipment Mfg. Ltd.), and was screened with a 24 mesh metal mesh. Each disintegrator, and magnesium stearate were further added to the resulting granulated substance, and were mixed in a bag. The resulting mixture was compressed with an ABM100S type static compressor (Tokyo Koki Seizosho, Ltd.), and tablets were produced.

Comparative Examples 10 to 12

Each poorly soluble drug, each disintegrator, magnesium hydroxide, magnesium oxide, sodium lauryl sulfate, D-mannitol, crystalline cellulose, hydroxypropyl cellulose, and magnesium stearate were mixed on a mortar, and a mixture powder was prepared.

TABLE 13

|  |  | Example 25 Comparative Example 10 | Example 26 Comparative Example 11 | Example 27 Comparative Example 12 |
|---|---|---|---|---|
| Poorly Soluble Drug | Ibuprofen | 100.0 | — | — |
| Poorly Soluble Drug | Mefenamic Acid | — | 125.0 | — |
| Poorly Soluble Drug | Ursodeoxycholic Acid | — | — | 50.0 |
| Alkaline Agent | Magnesium Hydroxide | 20.0 | 10.0 | 20.0 |
| Alkaline Agent | Magnesium Oxide | 8.8 | 4.4 | 8.8 |
| Surfactant | Sodium Lauryl Sulfate | 10.0 | 10.0 | 15.0 |
| Excipient | D-mannitol | 44.7 | 34.1 | 16.7 |
| Excipient | Crystalline cellulose | 50.0 | 50.0 | 30.0 |
| Binder | Hydroxypropyl Cellulose | 4.0 | 4.0 | 2.0 |
| Disintegrator | Crospovidone | 10.0 | — | — |
| Disintegrator | Carmellose Calcium | — | 10.0 | 6.0 |
| Lubricant | Magnesium Stearate | 2.5 | 2.5 | 1.5 |
|  | Total Amount (mg) | 250.0 | 250.0 | 150.0 |

Dissolution tests were conducted by replacing the 2nd fluid of the Japanese Pharmacopoeia Disintegration Test with a 50 mM phosphate buffer solution (with a pH of 5). The dissolution rates after 60 minutes the test began obtained by the dissolution tests are shown in Table 14. It was found that, although ibuprofen, mefenamic acid, and ursodeoxycholic acid were intrinsically poorly soluble in acid, by making them into the solubility improving tablet of the present invention, solubility in an acidic solution could be improved.

TABLE 14

|  | Ibuprofen | | Mefenamic Acid | | Ursodeoxycholic Acid | |
|---|---|---|---|---|---|---|
| Poorly Soluble Drug | Example 25 | Comparative Example 10 | Example 26 | Comparative Example 11 | Example 27 | Comparative Example 12 |
| Dissolution Rate (%) | 44.0 | 7.0 | 37.7 | 5.0 | 55.0 | 7.5 |

INDUSTRIAL APPLICABILITY

A solubility improving preparation of the present invention improves the solubility of drugs with low oral absorption due to poor solubility and mitigates the effects of pH conditions in the digestive organ to solubility, and thus it is extremely useful as a preparation for poorly soluble drugs with improved oral absorption.

The invention claimed is:
1. A solid preparation comprising:
(A) a granulated substance comprising
(i) a poorly soluble drug having a carboxyl group in the molecule,
wherein the poorly soluble drug is an optically active compound represented by Formula (I):

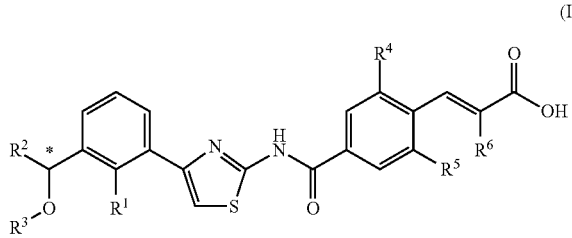

wherein,
$R^1$ is chosen from halogen atoms and $C_1$-$C_3$ alkyloxy groups;
$R^2$ is chosen from $C_1$-$C_8$ alkyl groups;
$R^3$ is chosen from $C_1$-$C_8$ alkyl groups;
$R^4$ and $R^5$ are each independently chosen from a fluorine atom and a chlorine atom;
$R^6$ is chosen from $C_1$-$C_3$ alkyl groups and $C_1$-$C_3$ alkyl oxy groups; and
the carbon atom with "*" attached to it is an asymmetric carbon, its pharmaceutically acceptable salt, or solvate thereof
(ii) an alkaline agent,
wherein the alkaline agent is chosen from magnesium oxide, magnesium hydroxide, hydroxylation alumina magnesium, synthetic hydrotalcite, calcium silicate and mixtures thereof,
wherein the alkaline agent is present in an amount of 0.5 to 30 weight % based on the weight of the granulated substance,
(iii) a surfactant,
wherein the surfactant is chosen from sodium lauryl sulfate, sucrose fatty acid ester and polyoxyethylene polyoxypropylene glycol,
wherein the surfactant is present in an amount of 0.2 to 50 weight % based on the weight of the granulated substance,
wherein the granulated substance does not substantially contain a disintegrator, and
(B) a disintegrator external to the granulated substance.
2. The solid preparation according to claim 1, wherein the poorly soluble drug is (S)-(E)-3-(2,6-dichloro-4-{4-[3-(1-hexyloxyethyl)-2-methyloxyphenyl]thiazole 2-yl carbamoyl}phenyl)-2-methylacrylic acid, its pharmaceutically acceptable salt, or solvate thereof.
3. The solid preparation according to claim 1, wherein the alkaline agent is magnesium oxide and/or magnesium hydroxide.
4. The solid preparation according to claim 3, wherein 0.5 to 30 weight % of magnesium oxide and/or 0.5 to 30 weight % of magnesium hydroxide are contained as alkaline agents based on the said granulated substance.
5. The solid preparation according to claim 1, wherein the surfactant is an ionic surfactant.
6. The solid preparation according to claim 5, wherein the ionic surfactant is a sulfuric acid ester salt.
7. The solid preparation according to claim 6, wherein the sulfuric acid ester salt is a sodium lauryl sulfate.
8. The solid preparation according to claim 1, wherein the disintegrator is chosen from cellulosic derivative, polyvinyl pyrrolidone derivative and starch derivative.
9. The solid preparation according to claim 8, wherein the disintegrator is chosen from a low substituted hydroxypropyl cellulose, carmellose calcium, crospovidone, and carboxymethyl starch sodium.
10. The solid preparation according to claim 9, wherein carmellose calcium is present in an amount of 0.2 to 30 weight % based on the weight of the solid preparation.
11. The solid preparation according to claim 10, wherein carmellose calcium is present in an amount of 3 to 7 weight % based on the weight of the solid preparation.
12. The solid preparation according to claim 1, wherein the granulated substance contains hydroxypropyl cellulose.
13. The solid preparation according to claim 12, wherein hydroxypropyl cellulose is present in an amount of 0.1 to 20 weight % based on the weight of the granulated substance.
14. The solid preparation according to claim 1, wherein magnesium oxide is present in an amount of 0.5 to 30 weight %, magnesium hydroxide is present in an amount of 0.5 to 30 weight %, sodium lauryl sulfate is present in an amount of 0.2 to 50 weight %, and hydroxypropyl cellulose is present in an amount of 0.1 to 20 weight % based on the weight of the granulated substance, and wherein the disintegrator is carmellose calcium present in an amount of 0.2 to 30 weight % based on the weight of the solid preparation.
15. The solid preparation according to claim 14, wherein the poorly soluble drug is (S)-(E)-3-(2,6-dichloro-4-{4-[3-(1-hexyloxyethyl)-2-methyloxyphenyl]thiazole 2-yl carbamoyl}phenyl)-2-methylacrylic acid, its pharmaceutically acceptable salt, or solvate thereof.
16. The solid preparation according to claim 14, wherein carmellose calcium is present in an amount of 3 to 7 weight % based on the weight of the solid preparation.
17. The solid preparation according to claim 1, wherein the solid preparation form is tablet or capsule.
18. The solid preparation according to claim 17, wherein the solid preparation form is tablet.
19. A process for producing the solid preparation according to claim 1 containing: (A) mixing (i) the poorly soluble drug having an acidic group in the molecule of claim 1, (ii) an alkaline agent, (iii) a surfactant, and granulating the mixture, (B) mixing the granulated substance prepared in (A) with a disintegrator, and (C) obtaining the solid preparation according to claim 1.
20. A method for improving the solubility of the poorly soluble drug having an acidic group in the molecule according to claim 1, wherein the method contains (A) mixing (i) the poorly soluble drug having an acidic group in the molecule, (ii) an alkaline agent, (iii) a surfactant, and granulating the mixture, (B) mixing the granulated substance prepared in (A) with a disintegrator, and (C) obtaining the solid preparation according to claim 1, wherein after mixing (B), the solubility of the poorly soluble drug according to claim 1 has improved solubility.

* * * * *